US010856764B2

(12) United States Patent
Dayeh et al.

(10) Patent No.: US 10,856,764 B2
(45) Date of Patent: Dec. 8, 2020

(54) METHOD FOR FORMING A MULTIELECTRODE CONFORMAL PENETRATING ARRAY

(71) Applicant: The Regents of the University of California, Oakland, CA (US)

(72) Inventors: Shadi A. Dayeh, San Diego, CA (US); Farid Azzazy, San Diego, CA (US); Sang Heon Lee, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 524 days.

(21) Appl. No.: 15/501,426

(22) PCT Filed: Aug. 7, 2015

(86) PCT No.: PCT/US2015/044185
§ 371 (c)(1),
(2) Date: Feb. 2, 2017

(87) PCT Pub. No.: WO2016/022906
PCT Pub. Date: Feb. 11, 2016

(65) Prior Publication Data
US 2017/0231518 A1    Aug. 17, 2017

Related U.S. Application Data

(60) Provisional application No. 62/034,265, filed on Aug. 7, 2014.

(51) Int. Cl.
*A61B 5/0478* (2006.01)
*B81B 1/00* (2006.01)
*B81C 1/00* (2006.01)

(52) U.S. Cl.
CPC ............. *A61B 5/0478* (2013.01); *B81B 1/00* (2013.01); *B81C 1/00111* (2013.01);
(Continued)

(58) Field of Classification Search
CPC ......... A61B 1/008; A61B 5/0031; A61B 5/05; A61B 5/6867; A61B 5/0478;
(Continued)

(56) References Cited

U.S. PATENT DOCUMENTS 3,089,483 A    5/1963   Sheatz
5,215,088 A    6/1993   Normann et al.
(Continued)

OTHER PUBLICATIONS

Interconnection Tecnology for Semiconductors on Thick, Flexible Kapton (R) Substrates , PhD dissertation by C. Mundt, (1997).*
(Continued)

*Primary Examiner* — Carl J Arbes
(74) *Attorney, Agent, or Firm* — Greer, Burns & Crain, Ltd.; Steven P. Fallon

(57) ABSTRACT

A preferred conformal penetrating multi electrode array includes a plastic substrate that is flexible enough to conform to cortical tissue. A plurality of penetrating semiconductor micro electrodes extend away from a surface of the flexible substrate and are stiff enough to penetrate cortical tissue. Electrode lines are encapsulated at least partially within the flexible substrate and electrically connected to the plurality of penetrating semiconductor microelectrodes. The penetrating semiconductor electrodes preferably include pointed metal tips. A preferred method of fabrication permits forming stiff penetrating electrodes on a substrate that is very flexible, and providing electrical connection to electrode lines within the substrate.

16 Claims, 34 Drawing Sheets

(52) U.S. Cl.
CPC .......... *B81B 2201/0292* (2013.01); *B81B 2203/0361* (2013.01); *B81B 2203/04* (2013.01); *B81C 2201/013* (2013.01)

(58) Field of Classification Search
CPC ... H01L 21/4814; H01L 21/4846; B81B 1/00; B81B 1/00111; B81B 2201/0292; B81B 2203/0361; B81B 2203/04; B81C 2201/013
See application file for complete search history.

(56) References Cited

U.S. PATENT DOCUMENTS

| | | | |
|---|---|---|---|
| 7,790,493 B2* | 9/2010 | Wise | H01L 21/4846 257/E21.215 |
| 9,159,635 B2* | 10/2015 | Elolampi | H01L 23/13 |
| 9,289,132 B2* | 3/2016 | Ghaffari | A61B 1/00082 |
| 9,554,484 B2* | 1/2017 | Rogers | A61B 5/01 |
| 9,936,574 B2* | 4/2018 | Rogers | A61B 5/6867 |
| 2003/0100823 A1 | 5/2003 | Kipke et al. | |
| 2006/0213259 A1 | 9/2006 | Prinz et al. | |
| 2007/0007240 A1* | 1/2007 | Wise | H01L 21/4846 216/13 |
| 2010/0298895 A1* | 11/2010 | Ghaffari | A61B 1/00082 607/3 |
| 2011/0034912 A1* | 2/2011 | de Graff | H01L 27/14687 606/21 |
| 2011/0054583 A1* | 3/2011 | Litt | A61B 5/0031 607/116 |
| 2011/0106229 A1 | 5/2011 | Ortmann | |
| 2011/0230747 A1* | 9/2011 | Rogers | A61B 5/05 600/377 |
| 2011/0233075 A1 | 9/2011 | Soleymani et al. | |
| 2012/0065704 A1 | 3/2012 | Kavasssery et al. | |
| 2012/0296444 A1 | 11/2012 | Greenberg et al. | |
| 2012/0323288 A1 | 12/2012 | Anderson et al. | |
| 2013/0072775 A1 | 3/2013 | Rogers et al. | |
| 2014/0303452 A1* | 10/2014 | Ghaffari | A61B 1/05 600/301 |

OTHER PUBLICATIONS

An Integrated Position-Sensing System for a MEMS-Based Cochlear Prosthesis, a PhD dissertation by J. Wang (2007).*

Fabrication and Modeling of Stretchable Conductors for Taumatic Brain Injury, a PhD dissertation by W. Cao (Jan. 2013).*
A Silicon Based, Three-Dimesional Neural Interface Manufacturing Processes for Intracortical Electrode Array, by Campbell et al (IEEE Trans. in Biomedical Engr. vol. 38, No. 8 Aug. 1991.*
Asano, Eishi, et al., "Origin and Propagation of Epileptic Spasms Delineated on Electrocorticography", Epilepsia, vol. 46, No. 7, (Jul. 2005), pp. 1086-1097.
Freeman, Walter, et al., "Spatial spectral analysis of human electrocorticograms including the alpha and gamma bands", Journal of Neuroscience Methods, vol. 95, Issue 2, Feb. 15, 2000, pp. 111-121, (12 pages).
Kim, B J, "3D Parylene sheath neural probe for chronic recordings", Journal of Neural Engineering, vol. 10, No. 4:045002, (2013), (16 pages).
Kim, Dae-Hyeong, et al. "Dissolvable films of silk fibroin for ultrathin conformal bio-integrated electronics", Nature Materials, vol. 9, No. 6, (Jun. 2010), pp. 511-517.
Roland, Jarod, L., et al. "Brain mapping in a patient with congenital blindness—a case for multimodal approaches", frontiers in Human Neuroscience, vol. 7, Article 431, (Jul. 2013), (10 pages).
Rousche, Patrick, J., et al. "Flexible polyimide-based intracortical electrode arrays with bioactive capability", IEEE Transactions on Biomedical Engineering, vol. 48, No. 3, (Mar. 2001), pp. 361-371.
Takeuchi, Shoji, et al., "3D flexible multichannel neural probe array", J. Micromech. Microeng., vol. 14, No. 1, (2004), pp. 104-107.
Copenheaver, Blaine, "Notification of Transmittal of the International Search Report and the Written Opinion of the International Searching Authority, or the Declaration", Patent Cooperation Treaty Application No. PCT/US2015/044185, United States Patent Office as the International Searching Authority, International Search Report completed Oct. 12, 2015, International Search Report dated Nov. 9, 2015, 9 Pages.
DR Kipke, et al., Silicon-Substrate Intracortical Microelectrode Arrays for Long-Term Recording of Neuronal Spike Activity in Cerebral Cortex IEEE Trans. on Neur. Sys. and Rehab. Eng., vol. 11, No. 2, 2003.
PK Cambell, et al., A Silicon Based Three-Dimensional Interface: Manufacturing Processes for an Intracortical Electrode Array, IEEE Trans. On Biomed. Eng., vol. 38, No. 8, 1991.
VS Polikov, et al., Response of Brain Tissue to Chronically Implanted Neural Electrodes, Journal of Neuroscience Methods, vol. 148, 2005, 1-18.

* cited by examiner

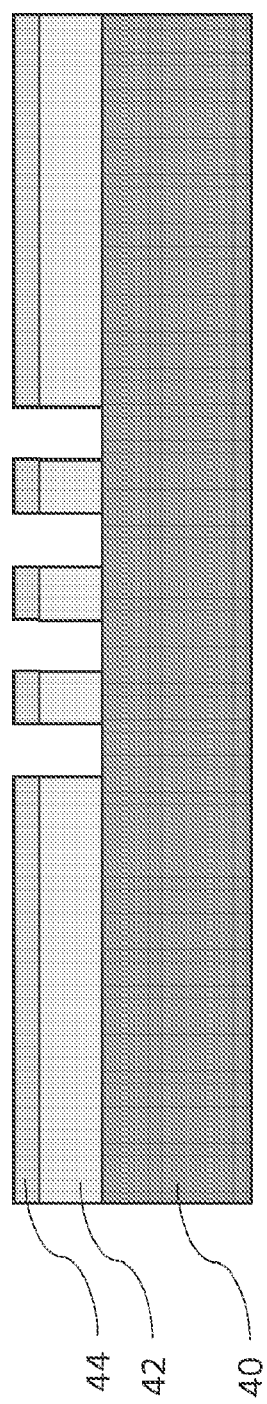

METHOD FOR FORMING A MULTIELECTRODE CONFORMAL PENETRATING ARRAY

PRIORITY CLAIM AND REFERENCE TO RELATED APPLICATION

The application claims priority under 35 U.S.C. § 119 and all applicable statutes and treaties from prior provisional application Ser. No. 62/034,265, which was filed Aug. 7, 2014.

FIELD

A field of the invention is sensors, and particularly cortical sensors. Example applications of the invention include neurological sensing via in vivo application of a sensor including a multi-electrode array to cortical tissue.

BACKGROUND

A widely used and minimally invasive neural recording modality is the EEG electrode. EEG (electroencephalogram) electrodes collect signals from the scalp. The EEG electrodes are small, flat metal disks that attach to the scalp. As a result, the EEG electrodes suffer from poor spatial resolution and provide a limited ability to determine neural activity below the topmost layers of the brain. Though EEG is a long-time and popular method for observing brain activity, firing patterns of individual neurons cannot be discriminated from EEG data. Though high-density recording cannot be collected with EEG electrodes, the EEG electrodes have nonetheless proven to be an important tool for diagnosing and treating epilepsy patients. The EEG electrodes are able to localize epileptic zones.

ECoG (Electrocorticography) electrodes have been tested for their ability to provide better resolution, but are much more invasive and potentially harmful to use in practice. See, e.g., Walter Freeman, et al, "Spatial spectral analysis of human electrocortigrams including the alpha and gamma bands," Journal of Neuroscience Methods, Vol 95, Issue 2, pp. 111-121 (2000); Jarod Roland, et al, "Brain Mapping in a patient with congenital blindness—a case for multimodal approaches," Frontiers in Human Neuroscience, vol. 31 (2013). ECoG electrodes record directly from the surface of the cortex. This greatly enhances the fidelity of the recorded signal and provides a higher signal to noise ratio because the skull and intermediary tissue no longer attenuate signals.

ECoG electrodes can be fabricated with thin film technology to achieve intimate contact with the gyri and sulci of the brain. These sensors have a large electrode pitch (center to center spacing between electrodes), typically on the order of about 1 cm. When designed with thin plastic substrates such as polyimide under about 10 µm, the thin film can be flexible enough to conform intimately to tissue. See, Dae-Hyeong Kim, et al, "Dissolvable films of silk fibroin for ultrathin conformal bio-integrated electronics," Nature Materials, Vol 9, 511-517 (2010). While higher performance than EEG is realized, the ECoG electrodes record local field potentials from groups of neurons. The recording of local field potentials is not conducive to resolving single unit activity. Eishi Asano, et al, "Origin and Propagation of Epileptic Spasms Delineated on Electrocorticography," Epilepsia, 46 (7) 1086-1097, (2005). These ECoG based sensors make intracranial subdural recordings from child patients with epileptic spasms. Such conformable bio-integrated electronics have been demonstrated with ultrathin films (less than about 10 µm). These conformable electronics have been non-penetrating, and are low in spatial density. These non-penetrating conformal electronics have been inadequate for 3D mapping of cortical tissue because the sensing electrodes lie on the surface of the cortex.

Penetrating micro electrode designs have also been developed and a studied. Two types of penetrating silicon arrays, referred to as the Michigan probes and Utah electrodes, have been widely utilized in research projects. The Utah electrodes were also successfully used in clinical trials. These devices provide valuable information, but are limited because they do not conform to cortical tissue. The semiconductor substrates have a Young's modulus in the range of about 130-180 GPa, an order of magnitude higher than the ECoG electrodes discussed above. This is a great mechanical mismatch with cortical tissues. The advantage gained is the provision of minimally penetrating electrodes in the Michigan and Utah electrodes, but only at the expense of the mechanical mismatch. The provision of rigid penetrating electrodes in these devices is based upon a fabrication process that also provides relatively stiff substrate that has a mechanical mismatch with cortical tissues. The relatively large and nonflexible structures are known to elicit a reactive tissue response in cortical tissue. These devices often suffer from diminishing device performance over time in clinical settings. A probable cause for the diminished performance is the reactive tissue response of the central nervous system and scarring to biological tissue from the implantation procedure. Nonetheless, these designs have received significant attention because the penetrating arrays provide the ability to discriminate single unit activity as well as local field potentials. Another limitation of these probe arrays is their non-scalability to dimensions that can cover multiple sub-cortical or the entire cortical surface due to their size (generally dimensions of the order of 100 µm) and resulting brain tissue deformation. This limits their utility to single subcortical surfaces.

Others have sought to provide more conformal penetrating electrode sensor arrays. See, e.g., B J Kim, et al., "3D Parylene sheath neural probe for chronic recordings," J. Neural Eng. 10 (2013); Shoji Takeuchi et al., "3D flexible multichannel neural probe array," Journal of Micromachining and Microengineering, Vol 14, 104-107, (2004); Patrick Rousche et al, "Flexible polyimide-based intracortical electrode arrays with bioactive capability," IEEE Transactions on Biomedical Engineering, Vol 48, No 3 (2001). The attempts to provide conformal penetrating electrode sensors have suffered from poor resolution and difficult implantation. Mechanical property mismatch with cortical tissue is reduced with flexible probes such as the parylene probes, but implantation is difficult with flaccid electrodes. Fabrication of these devices often involves manual processing steps making this process difficult to scale into large-scale manufacturing. Takeuchi addressed the penetrating problem with very large polyimide penetrating electrodes that had Ni plating. The electrodes were about 1.2 mm, and had a wide pitch of about 200 µm. Each long shank electrode had three recording sites. The process for forming this sensor array was a complicated process involving releasing and folding up the penetrating electrodes. This process is poorly suited to large scale manufacturing, and does not scale down well to provide high resolution.

It has been shown that films of silk fibroin conform very well to cortical tissue at a thickness of about 5 µm. Dae-Hyeong Kim, et al, "Dissolvable films of silk fibroin for ultrathin conformal bio-integrated electronics," Nature Materials, Vol 9, 511-517 (2010).

SUMMARY OF THE INVENTION

A preferred conformal penetrating multi electrode array includes a plastic substrate that is flexible enough to conform to cortical tissue. A plurality of penetrating semiconductor micro electrodes extend away from a surface of the flexible substrate and are stiff enough to penetrate cortical tissue. Electrode lines are encapsulated at least partially within the flexible substrate and connected to the plurality of penetrating semiconductor microelectrodes. The penetrating semiconductor electrodes preferably include pointed metal tips.

An embodiment is a method for forming a multielectrode conformal penetrating array. The method includes providing a semiconductor substrate; coating a face of the semiconductor substrate with a flexible material; patterning the flexible material for vias; patterning and forming electrode lines on the flexible material and contact pads through the vias; patterning an opposite face of the semiconductor substrate; and etching the semiconductor substrate to form penetrating semiconductor micro electrodes extending away from the opposite face. The flexible material is preferably plastic, and preferably polyimide.

A preferred conformal penetrating multi electrode array includes a plastic substrate that is flexible enough to conform to cortical tissue. A plurality of penetrating semiconductor micro electrodes extend away from a surface of the flexible substrate and are stiff enough to penetrate cortical tissue. Electrode lines are encapsulated at least partially within the flexible substrate and electrically connected to the plurality of penetrating semiconductor microelectrodes. The penetrating semiconductor electrodes preferably include pointed metal tips.

DESCRIPTION OF THE PREFERRED EMBODIMENTS

Figure 1:
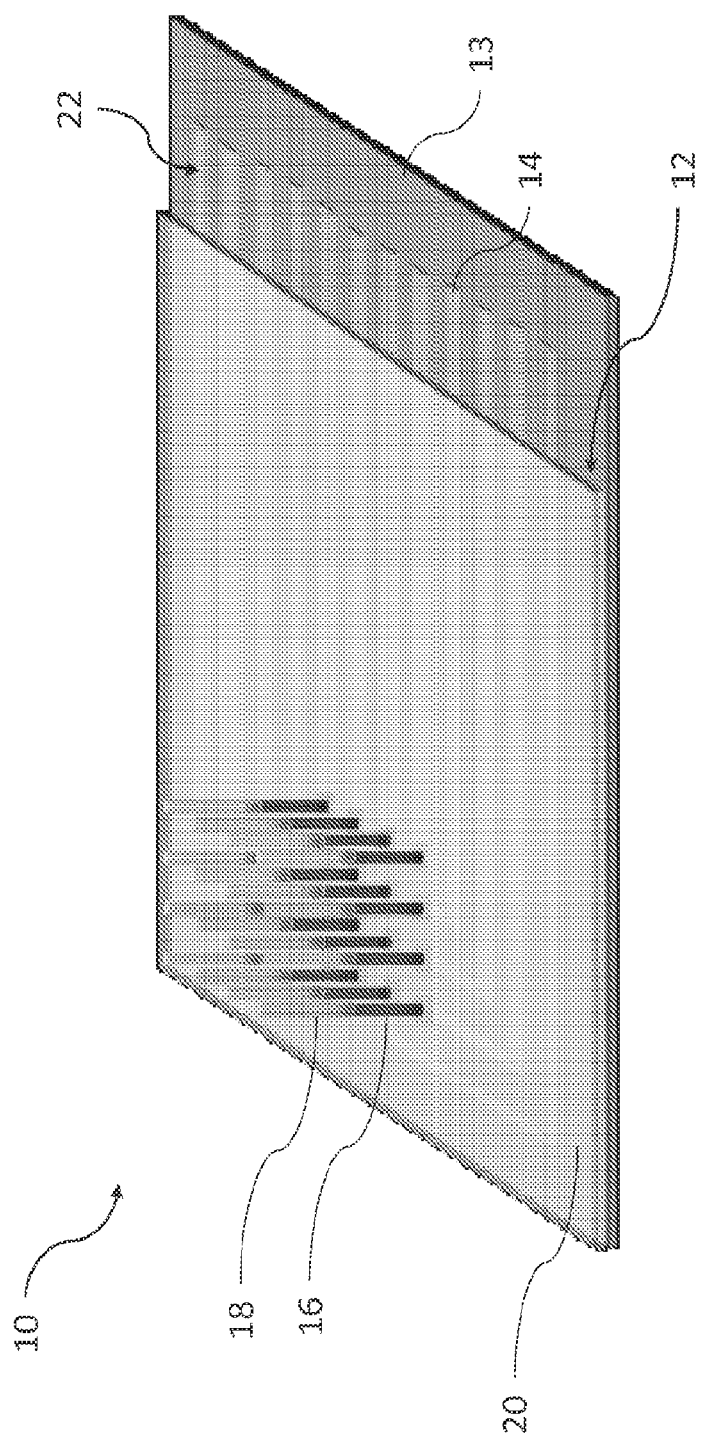
FIG. 1 is a schematic diagram of a preferred embodiment penetrating conformal multi electrode sensor array of the invention.

An embodiment of the invention is a penetrating multielectrode array on a thin film conformable substrate. The array can conform to cortical tissue, but provides stiff penetrating electrodes that can penetrate cortical tissues. Preferred embodiments provide a 3D electrode design with penetrating silicon micro electrodes. Preferred embodiments provide for separate addressability of penetrating electrodes through individual electrode lines of the thin film conformal substrate.

A preferred embodiment is a conformal penetrating multi electrode array that includes a flexible substrate, electrode lines encapsulated at least partially within the flexible substrate, and a plurality of penetrating semiconductor micro electrodes extending away from a surface of the flexible substrate and being electrically connected to provide signals to the electrode lines.

End portions of at least some of the electrode lines are preferably exposed for contact to another device. An electrode clip can be attached to the end portions.

Electrode lines preferably separately address single ones or groups of said plurality of penetrating semiconductor micro electrodes.

A preferred flexible substrate is a plastic substrate. A preferred plastic is polyimide. The semiconductor micro electrodes preferably are silicon, and preferably have a pointed tip, which is preferably metal. The penetrating electrodes are also preferably encapsulated in metal.

Preferred embodiments are an order of magnitude more flexible than the Michigan probes and Utah electrodes, which are formed on silicon substrates. Silicon has a Young's modulus of 130-180 GPa, while polyimide has a Young's modulus of 2.5 GPa. Other plastics can be used in the present invention. Generally, plastics having a Young's modulus equal to or less than 5 GPa are preferred. Plastics should be selected that resist silicon microprocessing techniques, are substantially more flexible than silicon, and scale down to ultrathin substrate thickness, tens of microns and most preferably 10 microns less.

In preferred embodiments, pitch between individual ones of said semiconductor micro electrodes is in the range of 25-200 µm, and more preferably 25-50 µm.

The flexible substrate preferably has a total thickness of tens of microns, and more preferably in the range of ~7-15 µm. Experiments showed that preferred fabrication processes can produce a total substrate thickness of down to ~7 µm. With polyimide, ~7-15 m provides excellent conformal behavior, while 7-10 µm is a most preferred range that closely matches and conforms to cortical tissue. Thicker substrates can be produced by the present fabrication process, e.g. 20, 30, 40 µm, and will still provide and array that greatly improve upon conformance compared to the Michigan probes and Utah electrodes. The fabrication process of the invention is also capable of producing much thicker substrates, should such substrates be desired.

The semiconductor penetrating electrodes are preferably arranged in a square pattern.

A height of said semiconductor micro electrodes is preferably ~30-120 µm, and most preferably ~70-100 µm.

An embodiment is a method for forming a multielectrode conformal penetrating array. The method includes providing a semiconductor substrate; coating a face of the semiconductor substrate with a flexible material; patterning the flexible material for vias; patterning and forming electrode lines on the flexible material and contact pads through the vias; patterning an opposite face of the semiconductor substrate; and etching the semiconductor substrate to form penetrating semiconductor micro electrodes extending away from the opposite face. The flexible material is preferably plastic, and preferably polyimide.

Preferred methods also include depositing an additional layer of flexible material over the electrodes prior to patterning an opposite face.

Preferred methods also include encapsulating the penetrating semiconductor micro electrodes.

A preferred conformal penetrating multi electrode array includes a plastic substrate that is flexible enough to conform to cortical tissue. A plurality of penetrating semiconductor micro electrodes extend away from a surface of the flexible substrate and are stiff enough to penetrate cortical tissue. Electrode lines are encapsulated at least partially within the flexible substrate and connected to the plurality of penetrating semiconductor microelectrodes. The penetrating semiconductor electrodes preferably include pointed metal tips.

Artisans will appreciate many benefits of preferred sensor arrays and fabrication processes. The present inventors are unaware of any prior fabrication process that provides for the combination of rigid penetrating electrodes, such as the Michigan probes or Utah electrodes, upon a substrate that mechanically matches or substantially matchers and conforms to cortical tissues. The present inventors are also unaware of any sensor array with a penetrating micro electrodes having a stiffness to penetrate cortical tissue combined with a flexible substrate that conforms to cortical tissue.

Preferred embodiment electrode arrays and sensors including arrays provide an increased spatial density of conformal surface electrodes by ten-hundred folds, while maintaining their sensitivity, compared to prior known devices discussed in the background. Preferred sensors combine ultrathin conformal electronics with an array of penetrating silicon micro-electrodes.

Preferred embodiment electrode arrays are flexible enough to conform to the surface of cortical tissue, while also providing stiff micro electrodes that readily penetrate into the cortical column. Preferred methods of fabrication overcome the challenge of heterogeneously integrating the penetrating micro electrode structures onto thin film plastic substrates. Preferred methods of fabrication are CMOS compatible processes that are readily amenable to mass fabrication.

Preferred embodiment electrode arrays and sensors have a reduced mechanical mismatch between the electrode interface and neural tissue compared to the Utah probe and Michigan electrode prior art discussed in the background. Arrays and sensors of the invention can therefore provide reduced tissue scarring compared to the prior art devices.

A preferred fabrication process fabricates rigid penetrating micro electrodes on thin film polyimide substrates. Other processes use similar plastics, and one example alternative is Parylene-C. Silicon penetrating electrode sensing elements are provided on the substrates. The preferred fabrication process is CMOS compatible process and provides silicon penetrating electrodes as a sensing element. This fabrication process heterogeneously integrates silicon microwires onto the polyimide substrate in an etch-back process. Preferred fabrication processes provide a double side aligned process for defining silicon penetrating electrodes onto flexible substrates.

Fabrication processes consistent with preferred embodiments were demonstrated experimentally to provide example linearly spaced arrays and square packed arrays. Example center-to-center penetrating electrode spacing (pitch) achieved in experiments was as low as 25 µm between silicon penetrating electrodes in the example square packed array design. In the experiments, spacing at 25, 35, 50, 100 150 and 200 µm pitches were obtained. Higher spacing and other spacing within the range of 25-200 µm are readily obtained by the preferred methods. Preferred arrays have an electrode pitch of 25-50 µm. Silicon micro penetrating electrode aspect ratio as high as 18:1 (length to diameter) was successfully implemented in an electrochemically functional device.

The thin film flexible substrate of preferred arrays allows for the electrode to make intimate contact with surrounding cortical tissue around sulci and gyri of the brain, and the silicon microwire sensing elements, which penetrate into the cortex, enable arrays of the invention to exceed spatial resolution of known arrays. Experimentally fabricated arrays of the invention were tested and found to have a resistance of few hundred kilohms, making them suitable for both local field potentials and single unit recordings.

An example experimental embodiment recorded signals from a 100×100 µm active area with electrodes arranged into a 4×4 array. Example experimental devices have been fabricated with total thicknesses of electrodes, substrate and passivation as low as 7 µm. Fabrications and testing of example devices demonstrated repeatability with consistent impedance measurements.

A preferred embodiment example fabrication method begins with an n-type <111> silicon wafer. Ultimately, the silicon electrode height is constrained by the wafer thickness, and is preferably about 30-120 µm. A semiconducting material other than silicon may be used, and the substrate thickness is preferably no thinner than the final electrode height. A passivation layer, which can be spun coated on the bottom side of the wafer, protects metal leads from being in direct contact with cortical tissue.

A suitable passivation material in preferred embodiments is polymide. Multiple polyimide layers can be spun coat and baked to realize a preferred passivation layer. The passivation layer is patterned by photolithography and etched to open vias, exposing the bottom side of the semiconductor wafer. In one preferred embodiment, the passivation layer is a polyimide film and an $O_2/CF_4$ plasma is used to etch the passivation layer.

In another embodiment, a plurality of polyimide layers are used and vias are etched with an $O_2$ plasma through a patterned Ti mask. The dimensions of the vias are optimally as small as possible. In one example experimental embodiment, the vias are optionally less than or equal to 1600 µm². In a separate example experimental embodiment, the patterned vias are as small as 400 µm². Metal electrode lines are then patterned by photolithography on the backside of the wafer, with the vias being at the ends of the metal lines. These metal electrode lines provide electrical addressability for each individual semiconducting sensing site.

A double side photolithography alignment is used in a preferred fabrication method to pattern a nickel etch mask on the top side of the wafer. Ni squares as small as 7×7 µm are aligned over the vias in the double side alignment procedure. In one embodiment, the accuracy of the double-side alignment constrains the minimum feature sizes of the device. The device can then be adhesively bonded with polyimide to an Si/SiO$_2$ carrier wafer. In one embodiment, the bonding process utilizes two spun coat polyimide layers, one on the carrier wafer, and one on the backside of the device. The two wafers are brought into contact and baked under pressure. In another embodiment, a film of photoresist is spun onto the carrier wafer, and the backside of the device is brought into contact with the photoresist film. The stack is then baked under pressure. At this point in the processing, there may be as few as three polyimide layers in one embodiment, and as many as six in another example embodiment. These examples provide device thickness between about 7-15 μm.

In a final step, platinum or some other conductive biocompatible metal is selectively sputtered onto the electrode sidewalls. Pt is preferred as it has been demonstrate to substantially lower impedance over a frequency range of interest. In general, this step lowers the electrode impedance in PBS solution. FIG. 2C shows repeatable impedance data collected on electrodes with platinum coated electrodes, and devices show impedances between 300 kΩ and 900 kΩ at 1 kHz in 1×PBS solution. The device is then lifted off from the carrier wafer in dilute BOE solution or mechanically peeled off the carrier with tweezers, and connected to an electrode clip (e.g. a ZIF-Clip®) to complete fabrication. The device maintains enough mechanical stability to be cut down to an appropriate size with a sharp knife.

A preferred embodiment sensor array includes metal electrode lines on a thin flexible film, with an overall flex thickness of 7-15 μm. At the tips of each electrode line extends a Si 3D electrode sensor perpendicularly away from the thin flexible film. Preferred example devices have been fabricated with an area as low as 100×100 μm.

Preferred arrays include a temporary adhesive on a backside away from the penetrating electrodes. The adhesive adheres to an insertion tool during surgery and can be dissolved with solution. Experiments showed that Polyethylene Glycol 4000 powder melted to form pellets which then acted as temporary adhesive between the backside of the device and an insertion tool. PEG can be removed easily with saline solution, or PBS (phosphate buffered saline).

Experiments have demonstrated preferred and repeatable processes for fabricating a penetrating electrode array on a conformable substrate. Devices have successfully been fabricated to completion with the preferred methods. Two preferred methods were demonstrated, one with linear arrays of penetrating electrodes and another with square arrays. Repeatable impedance measurements have been taken on devices with platinum coating, with electrode impedances ranging from about 300 kΩ to 900 kΩ at 1 kHz. The SEM photographs below show two different embodiments of the current invention.

Preferred fabrication processes overcome significant challenges. Commonly used microfabrication techniques such as dry etching, annealing, and photolithography are extremely difficult to perform when thin plastic substrates are used, such as polyimide, due to chemical and thermal stability. Furthermore, the mechanical stability of flexible substrates with thicknesses that are less than twenty and especially less than ten micrometers pose further challenges making simple fabrication techniques such as photolithography or dry etching difficult. To provide an array of the invention, penetrating micro electrodes must also be properly aligned onto thin film substrates. Preferred fabrication processes overcoming difficulties encountered in performing photolithography with electrode structures already defined.

Preferred fabrication processes heterogeneously integrate micro fabrication processes. Without being bound by the theory, a preferred fabrication process is believed to be the first double side aligned process for defining semiconductor penetrating electrodes onto flexible substrates and providing electrode lines that connect to the electrodes. The preferred process permits down scaling of the penetrating electrodes and penetrating electrode spacing.

Preferred embodiments of the invention will now be discussed with respect to the drawings and with respect to experiments that demonstrate preferred fabrication processes and preferred flexible penetrating multielectrode array sensor devices of the invention. The experiments will be understood by artisans in view of the general knowledge in the art and the description that follows, and will also demonstrate broader aspects of the invention to artisans. In the description of preferred fabrication processes, schematic drawings are used that will be understood. Features may be exaggerated in some drawings for emphasis, and features may not be to scale.

FIG. 1 shows a preferred embodiment penetrating conformal multi electrode sensor array 10 of the invention. The sensor array includes a thin film plastic substrate 12, having a lower layer 13. In preferred embodiments, the thin film substrate 12 is polyimide. Other suitable exemplary plastics include parylene-C or any polymeric material that can be deposited conformably from gas or liquid sources. A pattern including a plurality of independent electrode lines 14 is upon the substrate and the individual electrode lines electrically connect to corresponding individual penetrating electrodes 16 that extend away from the substrate 12. A top portion of the penetrating electrodes is coated with metal 18, preferably Pt or Ti. The electrode lines are encapsulated with encapsulation layer 20 in areas of the array 10 that will make contact with tissue when implanted. The encapsulation layer 20 along with the lower layer 13 completes the flexible substrate. The encapsulation 20 leaves ends of the electrode lines 14 exposed to provide a contact region 22 of the electrode lines to permit measurement of signals from the lines 14.

Figure 2A:
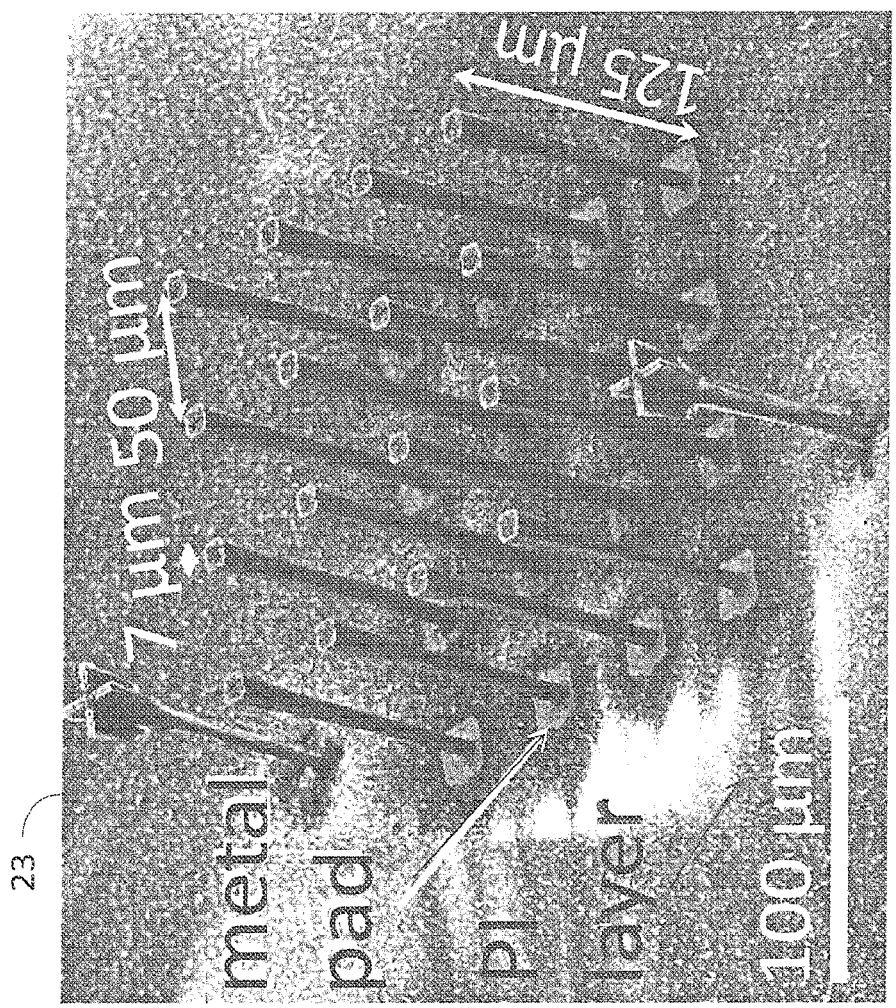
FIG. 2A is an SEM image of an experimental example multi electrode sensor array consistent with the FIG. 1 embodiment.
Figure 2B:
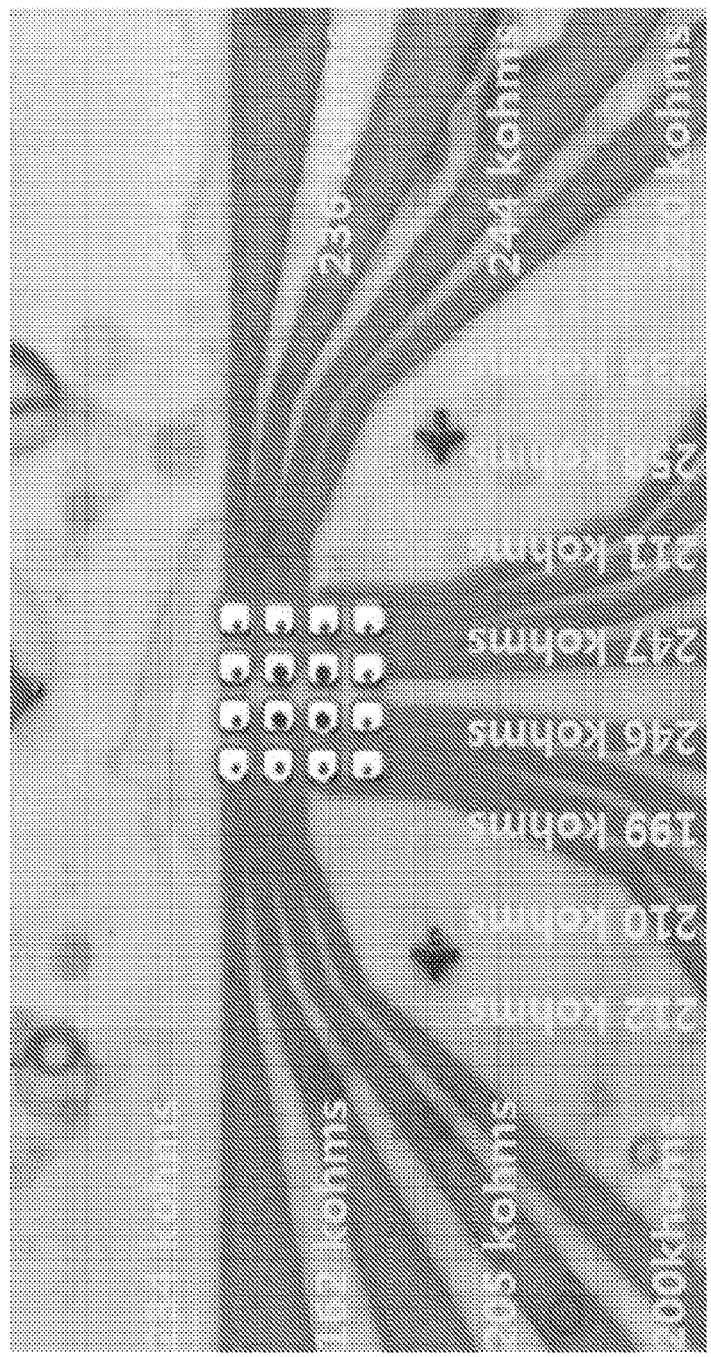
FIG. 2B is an optical microscope image of the electrode wire pattern of the FIG. 2A experimental sensor array.
Figure 2C:
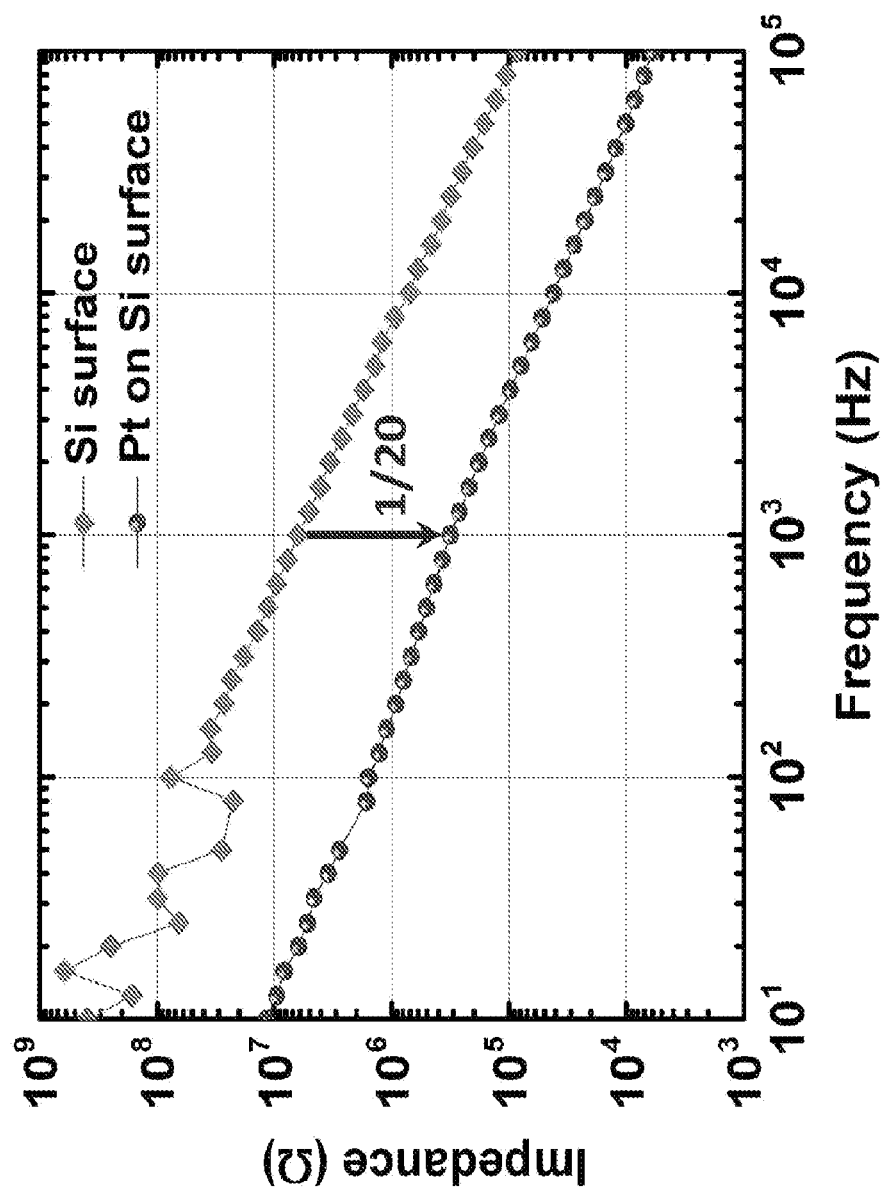
FIG. 2C is a data plot illustrating the electrode impedance of example bare silicon penetrating electrodes compared to Pt coated silicon penetrating electrodes over a range of frequencies.
Figure 2D:
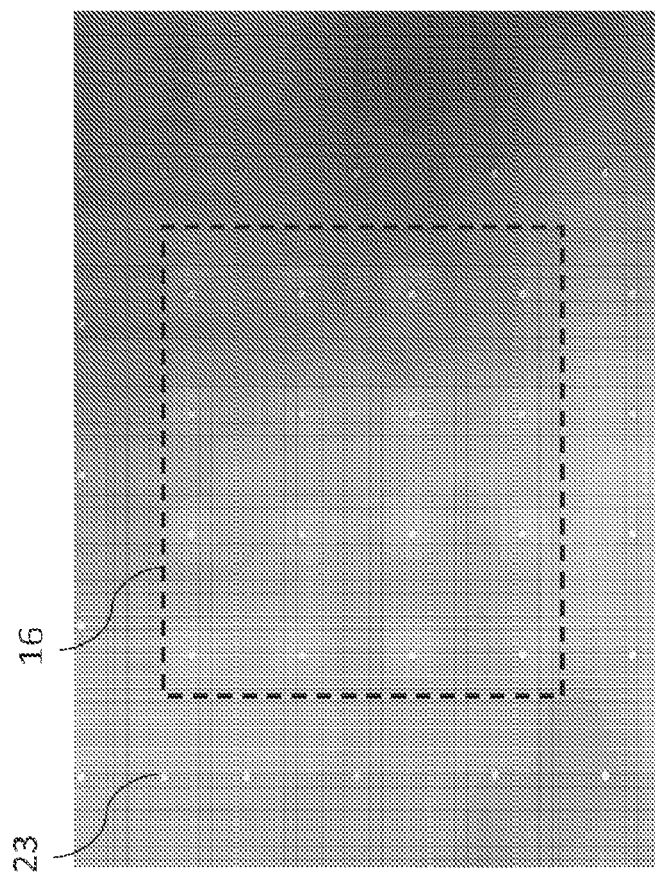
FIG. 2D is an image that shows a 4×4 pattern of penetrating active electrodes surrounded by a pattern of sacrificial electrodes.

FIG. 2A is an SEM image of an experimental example multi electrode sensor array consistent with the FIG. 1 embodiment. The SEM image is labelled with example dimensions, which can be varied according the fabrication process of the invention. In the illustrated example, the penetrating electrodes had a height of 125 μm and a diameter of 7 μm, with a spacing between electrodes of 50 μm. FIG. 2A also illustrates cross-shaped alignment marks/sacrificial electrodes (with a cross shaped end to aid alignment during processing) and FIG. 2D illustrates a pattern of sacrificial electrodes 23. These sacrificial electrodes can be formed in any pattern around the active penetrating electrodes to aid alignment during fabrication steps. The sacrificial electrodes also serve to protect the active penetrating electrodes during handling of the sensor array prior to implantation of the array. The sacrificial/alignment electrodes should not be longer than the penetrating electrodes. The sacrificial electrodes are easily removed, for example with a micromanipulator and microtip prior to implantation of the sensor array. The sacrificial electrodes 23 also serve to protect the active sensing microwire array from over etching during a preferred RIE/ICP etch process used during fabrication of the array. FIG. 2B is an SEM image of the electrode wire pattern of the FIG. 2A experimental sensor array. Example center to center penetrating electrode spacing (pitch) provided by fabrication methods range from 25 to 200 μm and higher. The measured resistance of each electrode and wire is labelled in FIG. 2B. The impedances can be adjusted by different surface metal or salt coatings. The electrode impedances measured in experimental examples ranges from 150 to 300 Kohms for Ti coated penetrating electrodes. The preferred method for depositing the surface metal coating is sputtering. However, other techniques can be applied including, for example, directional electron beam deposition, electrodeposition, and spin-casting and lift-off. Coating of the side walls of the penetrating electrodes can be achieved by loading an array onto an electrode beam deposition chuck at an angle. Experiments shows that sputtered coatings provided the lowest impedance for example Pt coatings of 50 nm thickness. Other preferred embodiments include Ti coatings. The Ti coating provided easier lift off of a protective PMMA later used during etching of native oxide during fabrication. FIG. 2C illustrates the measured impedance versus frequency range for bare silicon penetrating electrodes and silicon electrodes coated with Pt. FIG. 2D shows a pattern of 4×4 active penetrating electrodes 16 (central square pattern of 16 electrodes) surrounded by a pattern of sacrificial electrodes 23.

Figure 3A:
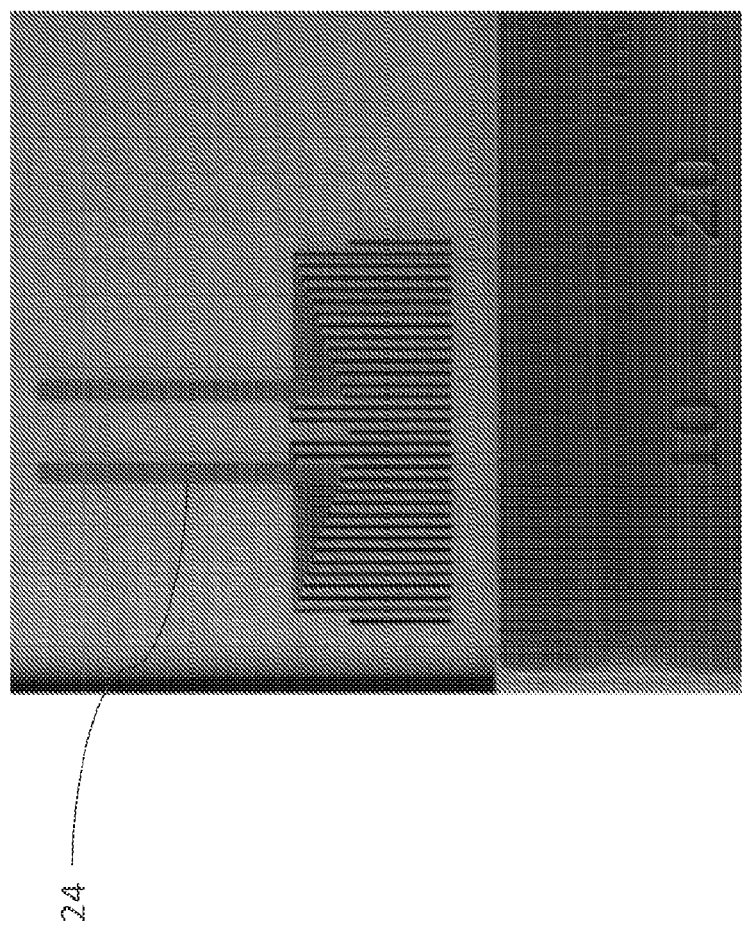
FIG. 3A is an image of a multi-fin experimental example multi electrode sensor array consistent with the FIG. 1 embodiment.
Figure 3B:
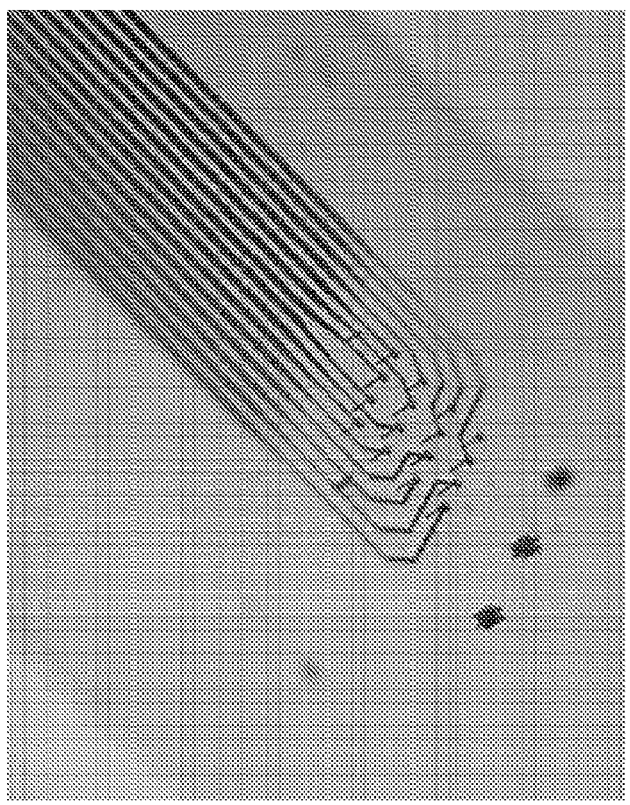
FIG. 3B is another image of the FIG. 3A multi-fin experimental example multi electrode sensor array consistent with the FIG. 1 embodiment prior to completion of the fabrication.
Figure 3D:
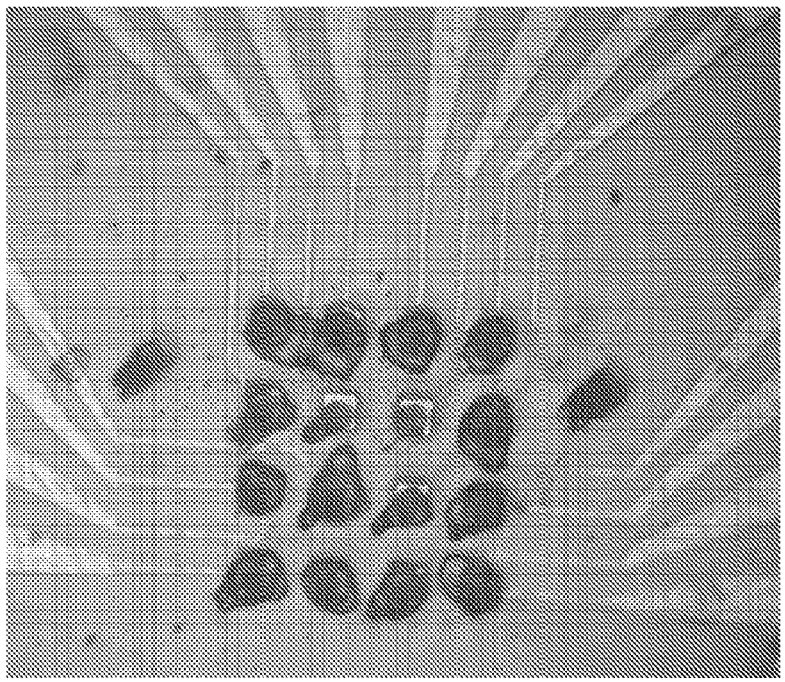
FIGS. 3C and 3D are comparative images showing two different experimental arrays with respective pitches of 25 µm and 50 µm between penetrating electrodes.
Figure 3C:
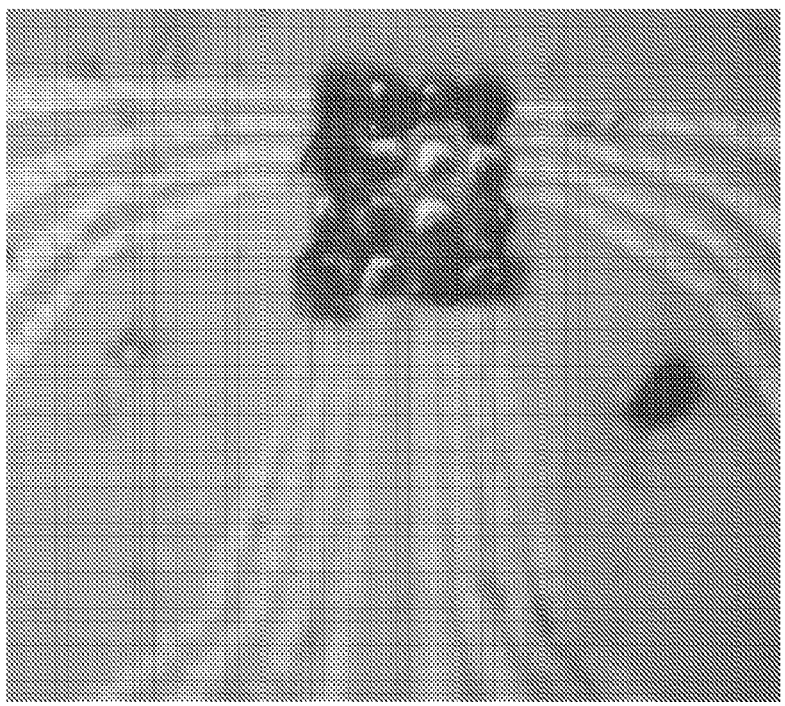

FIG. 3A illustrates a variation of the FIG. 1 embodiment, where two fins 24 connect groups of electrode lines. This experimental embodiment is especially useful for multicortical surface probing. The image is shown with a millimeter scale to indicate that the overall width of the pattern is about 17 µm. FIG. 3B shows another image of the array of FIG. 3A prior to formation of the fins. The fins are formed by trimming the plastic substrate at the end of the entire fabrication process to form two fins that can then sense separate portions of the brain through a different group of penetrating electrodes. Excess polyimide can be cut off with a sharp blade at the end of the fabrication. For example, some polyimide gets cut near the edge so that the device can fit into the ZIF clip. FIGS. 3C and 3D are comparative images showing two different experimental arrays with respective pitches of 25 µm and 50 µm between penetrating electrodes.

A preferred fabrication process will now be discussed. The preferred process avoids creating stresses that can cause buckling. Passivating leads with an insulating film such as $SiO_2$ or SiN on a device surface late in the process flow as a common practice in the art, after penetrating electrodes are defined, is avoided. Such films of oxide or nitride will cause mechanical stress on the flexible substrate, which may cause the substrate to curl or buckle. The final device thickness of the conformal substrates of preferred embodiments is so thin that even small amounts of tension or compression can be significant. The preferred process provides for access vias that are patterned into the passivation layer early in the process, granting electrical access to the silicon wafer through the backside of the device. The passivation layer is made of plastic/polymer, such as polyimide, to complete the flexible substrate with common material, thus minimizing the mechanical stress mismatch between differing materials. The use of plastic substrates such as polyimide further constrains processing implementations. Flexible plastic substrates cannot be annealed at high temperatures, prohibiting solid state bonding and CVD growth of silicon microwires. Furthermore, there exists a thermal coefficient mismatch between silicon and polyimide. The preferred fabrication process overcomes such issues with low temperature adhesive bonding techniques utilizing spin-on polymers such as photoresist or polyimide instead of solid-state bonding. Penetrating electrodes are not grown by CVD, but are instead etched back onto pre-patterned flexible substrates.

Figure 4A:
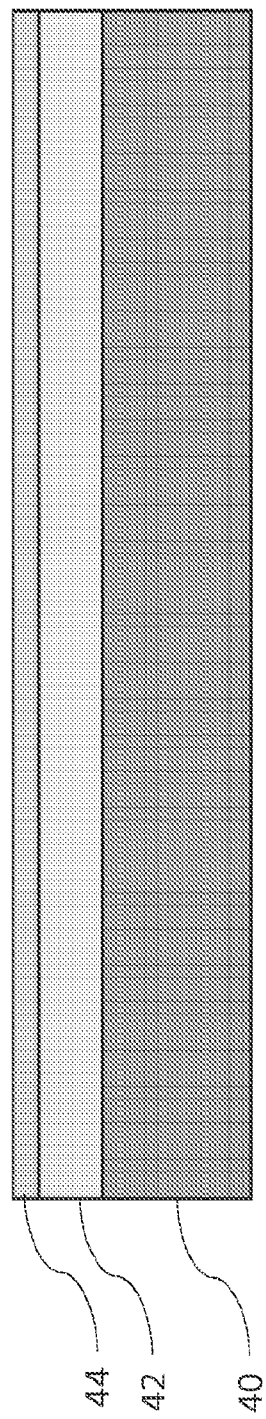
FIGS. 4A-4U are schematic diagrams illustrating a preferred fabrication process of the invention for making penetrating conformal multi electrode sensor arrays of the invention that are consistent with FIG. 1.

With reference to FIG. 4A, the preferred process begins with a semiconductor substrate 40. In experiments, a clean <111> silicon substrate was used but other semiconductors can be used in place of the silicon substrate. A thin film of flexible plastic/polymer 42 is deposited on the substrate 40. Polyimide is a preferred plastic, and spin coating a preferred deposition technique. This layer 42 sill serve as the passivation layer 20 in FIG. 1. Example experiments applied two spin coats of PI-2610. Two spin coats results in a thickness of 5 µm, which accounts for about one third to one half of the ultimate thickness of the thin film flexible substrate 12.

Figure 4B:
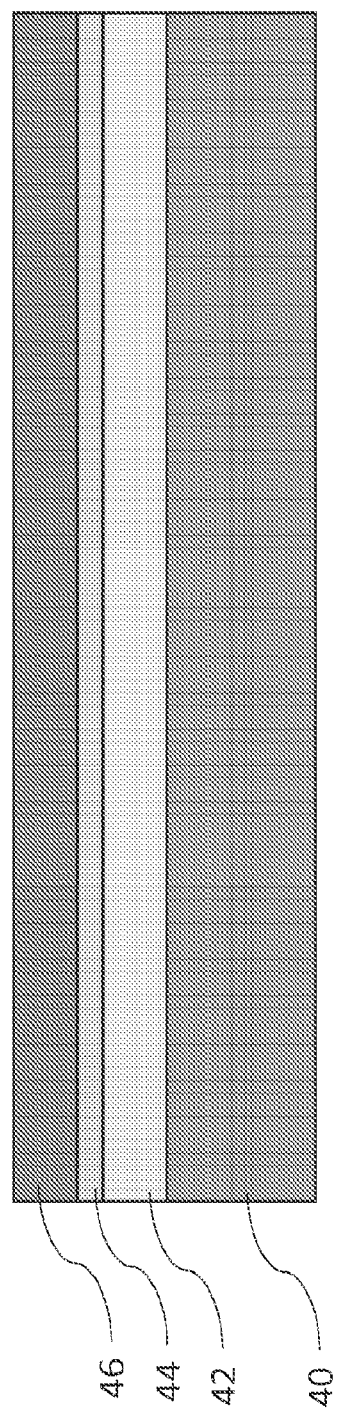
Figure 4C:
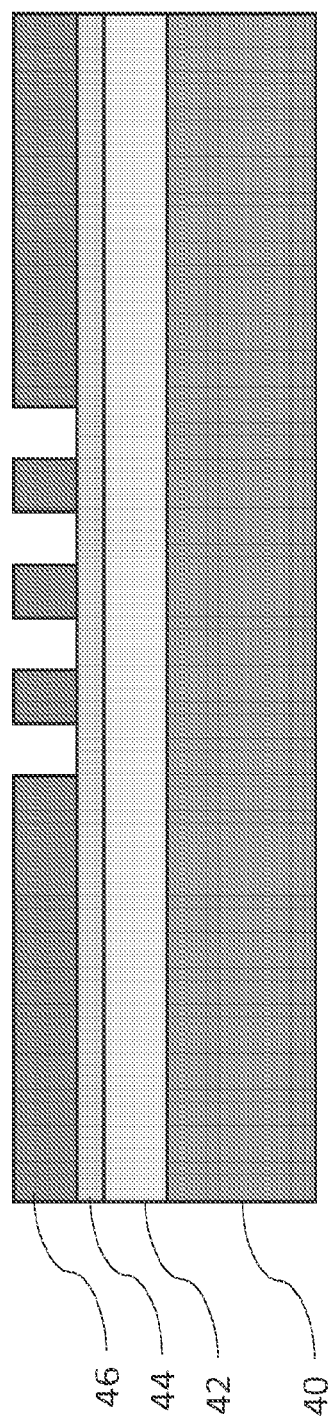
Figure 4D:
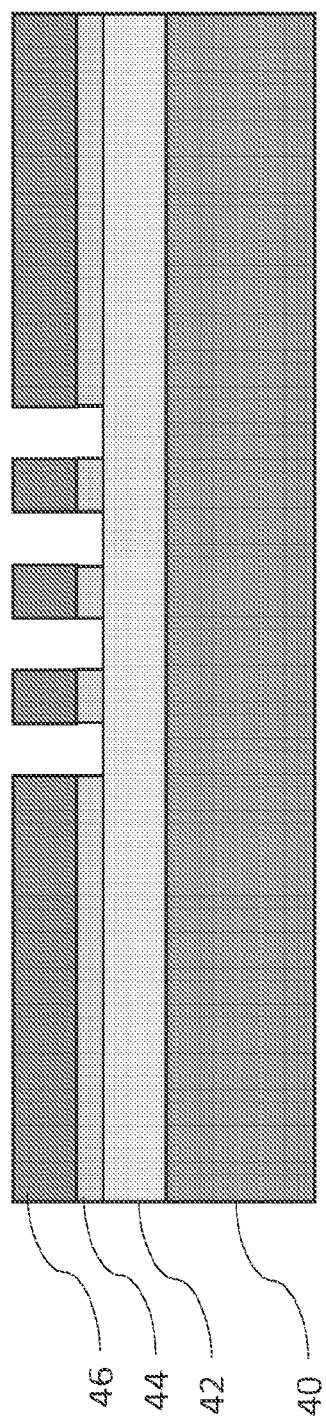
Figure 4F:
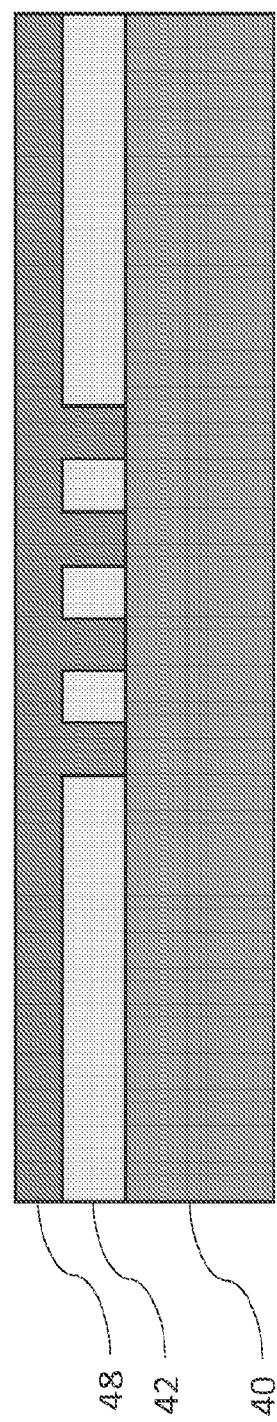
Figure 4G:
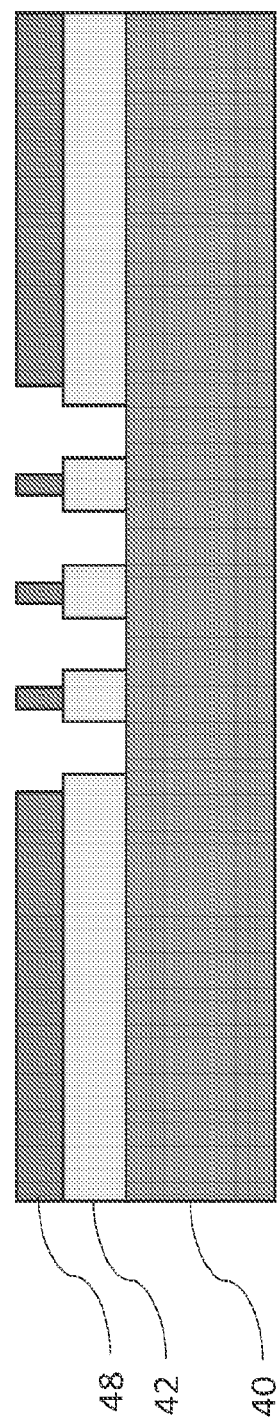

A sacrificial layer 44 of metal is deposited on the thin film plastic 42. Example experiments deposited a 20 nm sacrificial layer of titanium via electron beam deposition. In FIG. 4B a photoresist layer is deposited, such as by spin coating. Experiments used NR9-3000PY photoresist. Photolithography patterns openings in the photoresist in FIG. 4C and access vias are etched in the sacrificial film 44 in FIG. 4D. Example experiments etched the vias via dry etching in $Ar/SF_6$ plasma. Wet etching is limited to weak acids so dry etching is implemented in many process steps. After removal of the photoresist 46, the thin film plastic 42 is etched in FIG. 4E through the openings that had been created in the sacrificial layer 44. In experiments, a polyimide plastic was dry etched in $O_2$ plasma. In FIG. 4F, photoresist 48 is deposited after removal of the sacrificial film 44 on the plastic thin film and in the openings that had been created. In experiments, NR9-3000PY photoresist was deposited. HF dip is preferably used to etch away the sacrificial Ti layer, leaving access vias patterned into the PI passivation layer. This enables electrical connectivity to predefined regions of silicon in later metallization steps, while the rest of the metal line is passivated by plastic. This photoresist 48 is patterned in FIG. 4G for the deposition of electrode lines.

Figure 4H:
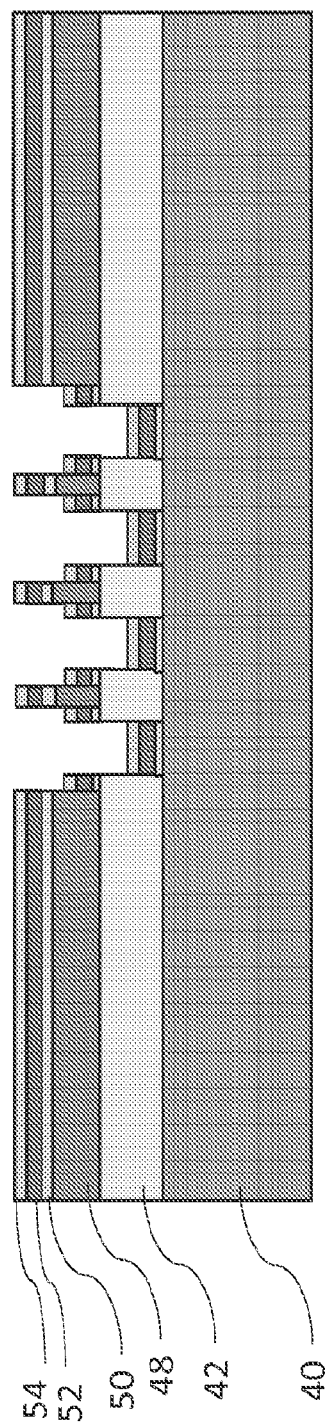

FIG. 4H shows the result of deposition of three layers of metal 50, 52 and 54, which is preceded preferably by an HF dip to remove native oxide from the silicon 40. In an example experiment, respective layers of 20 nm of Ti, 80 nm of Ni and 50 nm of Cr were deposited by electron beam evaporation. The Ni protects the Ti during later etching. Ni could be used as single layer, but the multi-layer with a Ti is preferred with an Si substrate as the Ti makes better ohmic contact to Si than Ni. Sputtering is preferred over electron beam deposition so that titanium is deposited on the sidewalls of the passivation layer, ensuring an electrical connection between the discontinuous metal layers on the surface of the Si substrate at the bottom of the via and on the surface of the polyimide layer. Other metals can be used. The selected metal used a seed layer (layer 50) should make good ohmic contact to the semiconductor 40. The metals selected should also have good etch selectivity because the surface of some metal will be exposed later in the processing, as in FIG. 4Q.

Figure 4I:
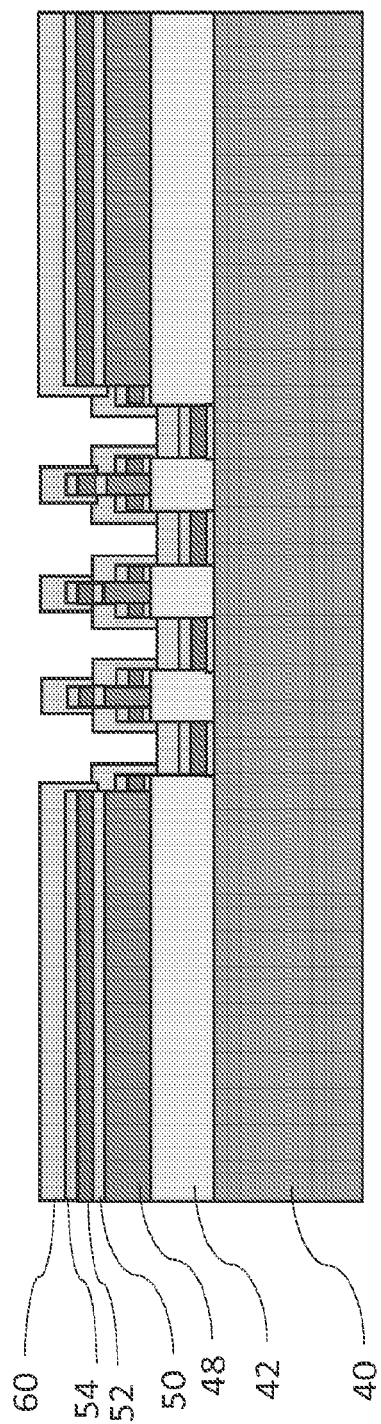
Figure 4J:
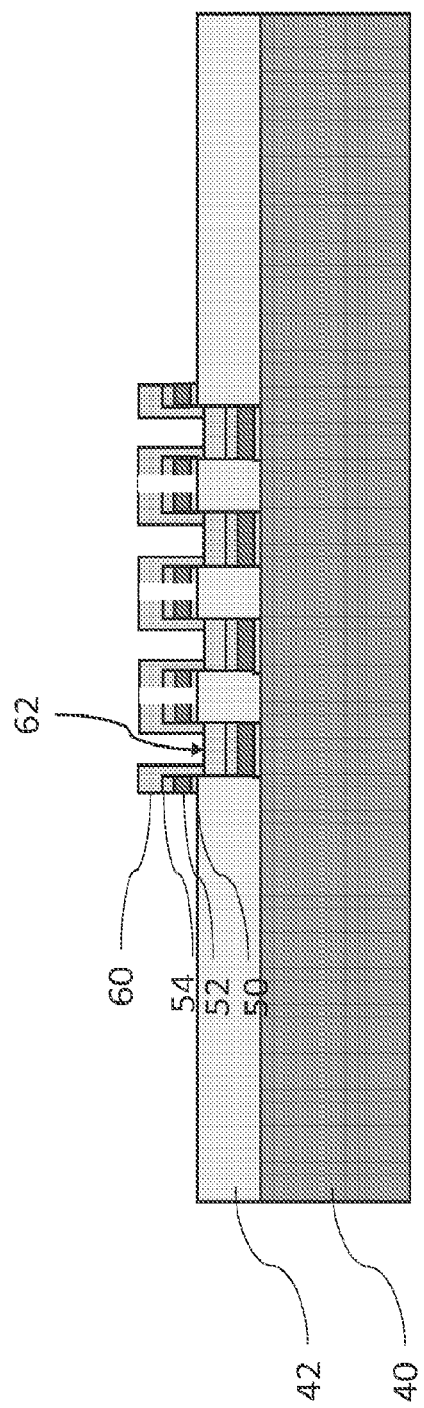

FIG. 4I illustrates deposition of a thick final layer of metal 60 for the electrode lines. In an example experiment, this final layer 60 was 250 nm of Ti deposited via sputtering. FIG. 4J illustrates completion of the lift-off of the photoresist 48, which leaves the multilayer patterned electrode lines, formed by layers 50, 52, 54 and 60 patterned on one side of the plastic layer 42 with contact through to the semiconductor substrate 40 in via holes 62.

Figure 4K:
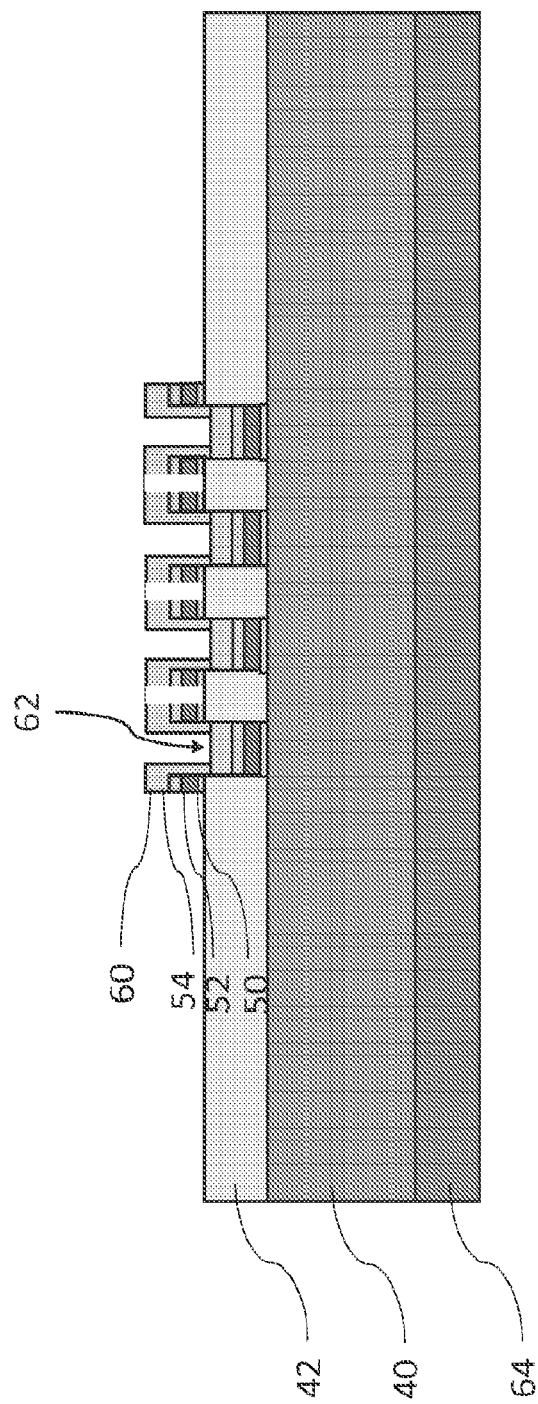
Figure 4L:
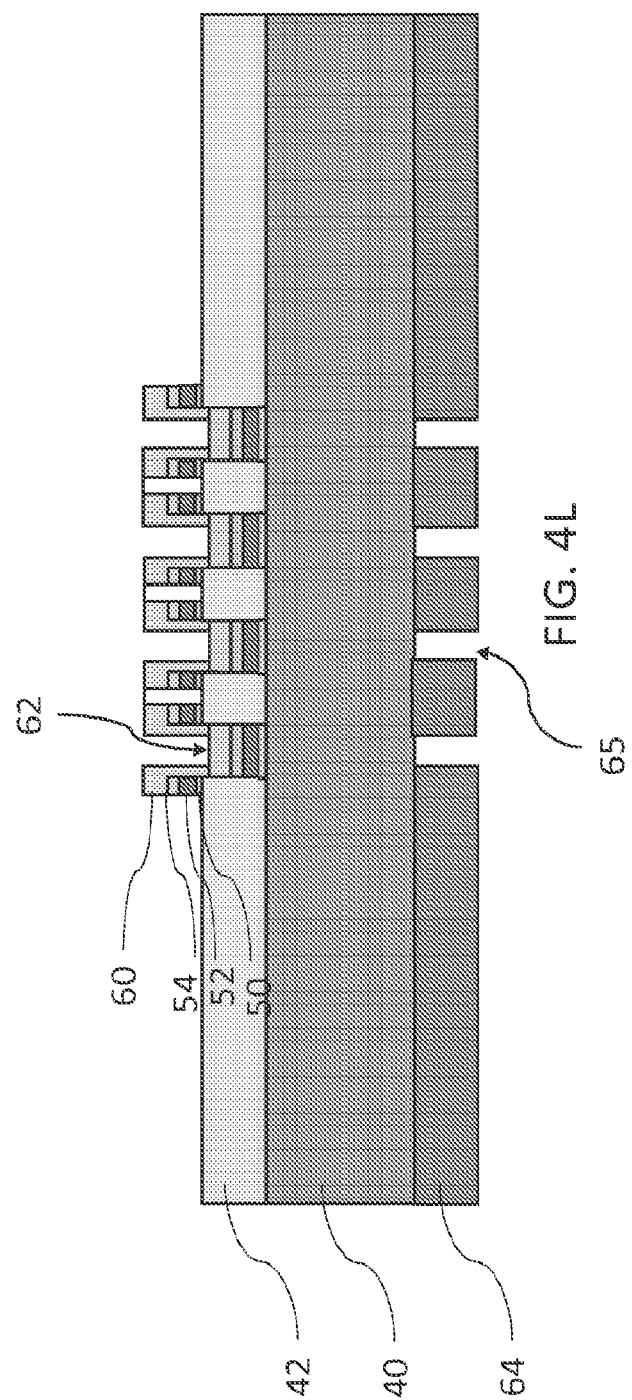

FIG. 4K illustrates the commencement of processing on an opposite side of the substrate 40 to form the penetrating electrodes. The same orientation is maintained as in other figures for consistency and simplicity of illustration, while artisan will appreciate that the partially complete fabrication of FIG. 4J can be flipped for further processing in FIG. 4K and those that follow. A layer of photoresist 64 is deposited in FIG. 4K, and then is patterned in FIG. 4L to form access vias 65. This patterning is conducted with double-side alignment to the metal dot (Ni layer 50 in via 62), which will ensure contact between the penetrating electrodes to be formed from processing of the substrate 42 and the electrode lines formed of the multiple metal layers 50, 52, 54 and 60. The double side alignment process allows one to align and expose patterns on the top-side of the substrate 42 to alignment markers or features on the bottom-side. Experiments showed that square spaced arrays permitted more precision in the double sided alignment process. The accuracy of the double side alignment was improved in experiments when square packed arrays were implemented because the alignment of the etch mask was less sensitive to rotation misalignments. Furthermore, higher density silicon microwires could be defined in 4×4 arrays compared to linearly spaced arrays with spacing as low as 25 µm being successfully implemented.

Figure 4M:
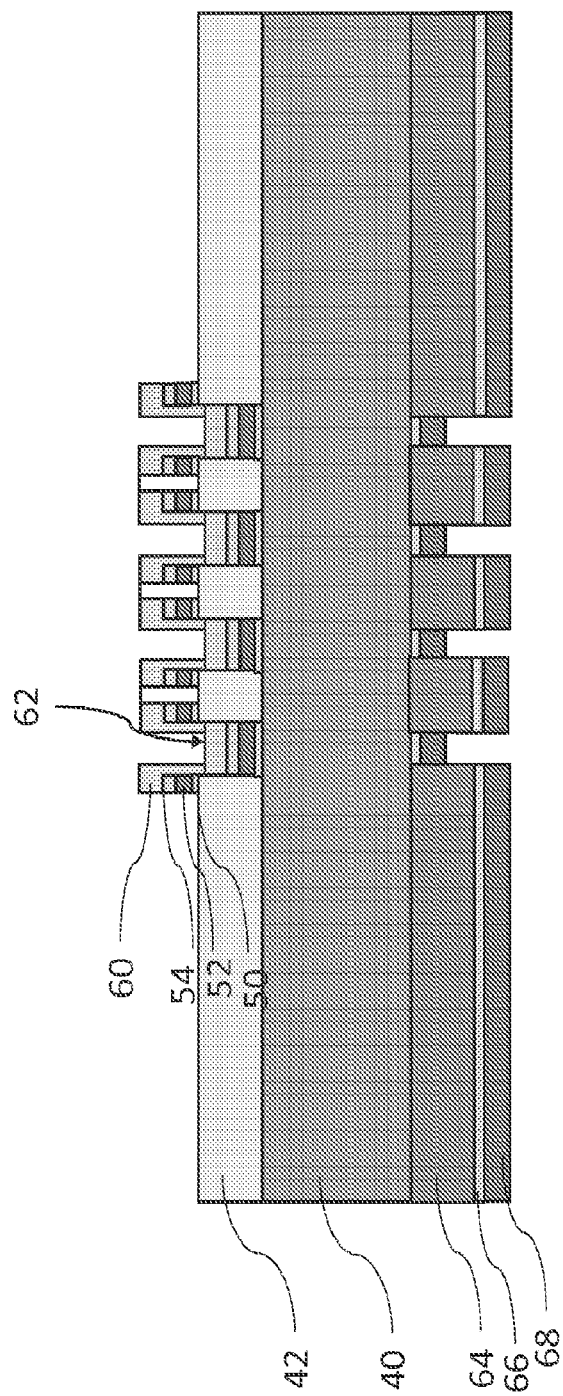
Figure 4N:
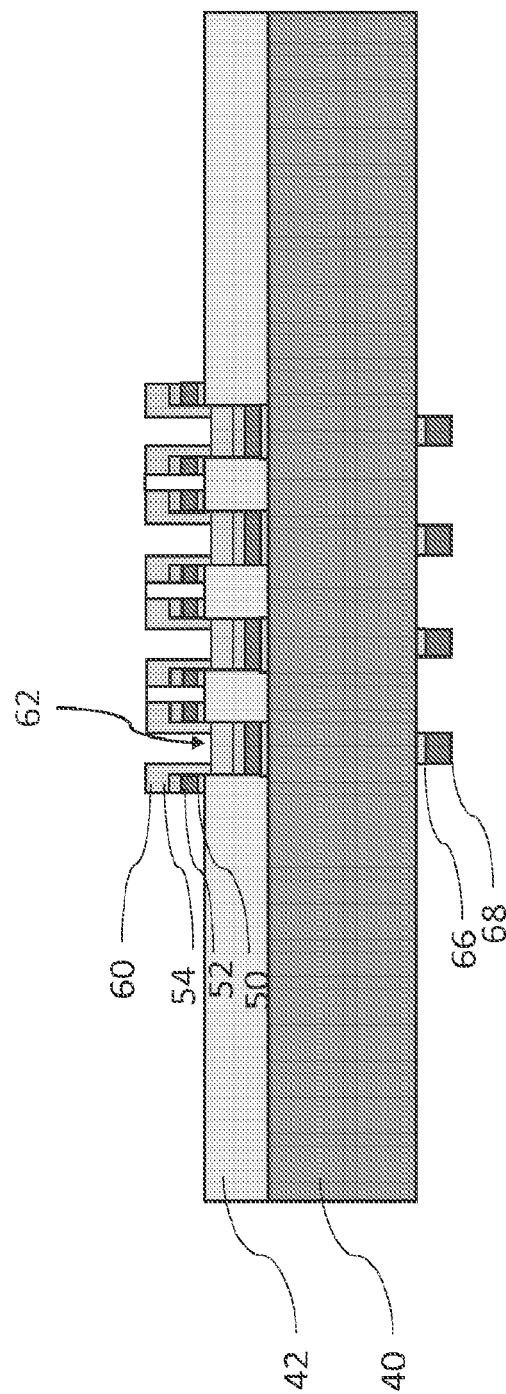
Figure 4O:
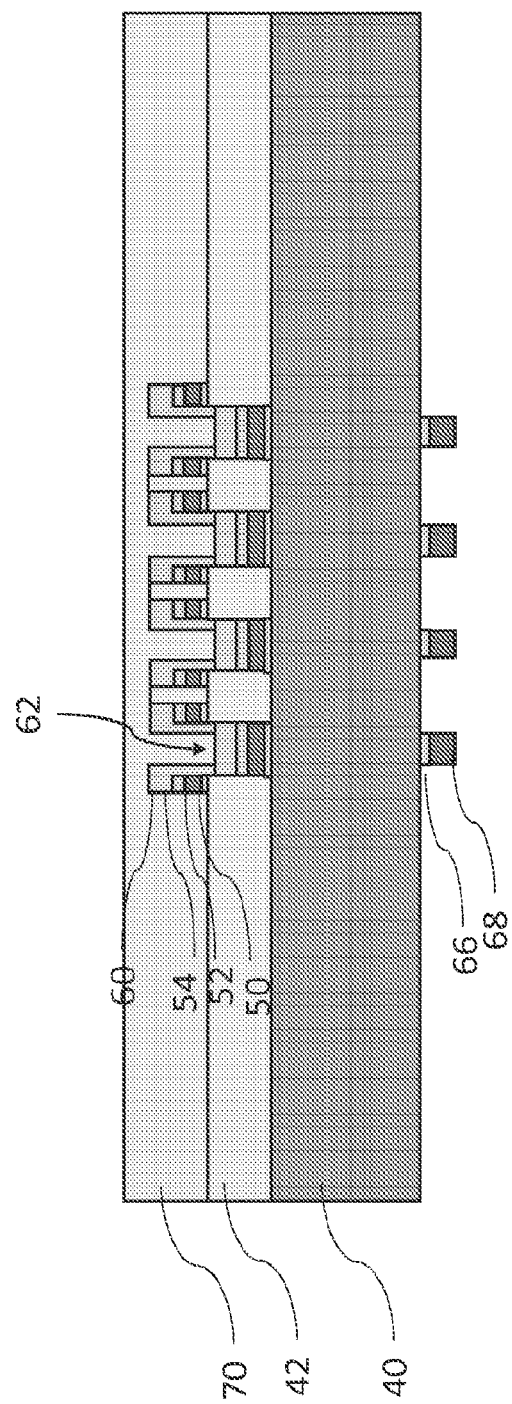

In FIG. 4M metal layers 66 and 68 are deposited. Ti is again preferred as layer 66 for contact when the substrate 40 is silicon. In an example experiment, a 20 nm Ti layer was deposited as a contact layer by electron beam evaporation followed by a 60 nm layer of Ni. Lift-off of the photoresist 64 leaves a pattern of metal of the layers 66 and 68 at planned locations of the penetrating electrodes, as shown in FIG. 4N. In FIG. 4O, additional plastic 70 is deposited that forms the lower portion 13 of the substrate 12. In example experiments the additional plastic was formed by spin coating and curing of PI-2610. Polyimide is not etch-selective to strong acids, so aggressive cleaning solutions such as piranha or RCA should be used before the additional plastic 70 is spun coat onto the device.

Figure 4P:
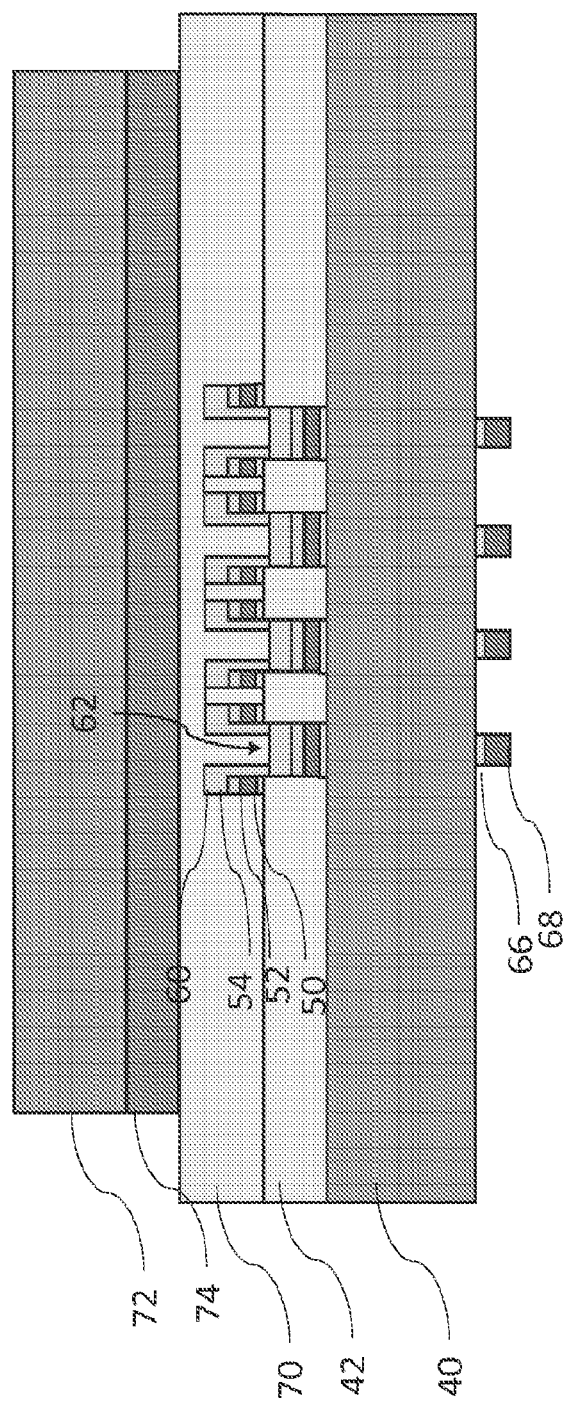
Figure 4Q:
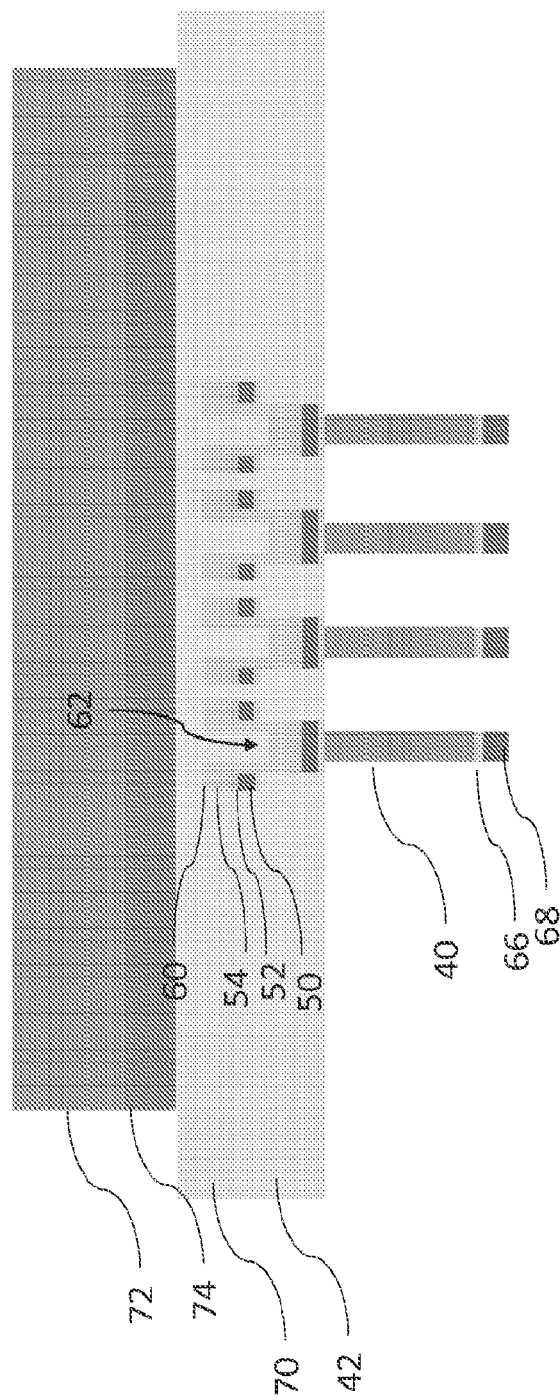

A carrier substrate 72 prepared with a photoresist layer 74 is then adhered to the plastic layer 70, followed by a soft bake that evaporates solvent out of the photoresist and improves adhesion, e.g. 1 min at 150° C., as shown in FIG. 4P. Photoresist was shown to provide reliable bonding, but other bonding materials that provide a reliable and intimate bond without air pockets or bubbles that would stress. Handling the thin electrode array is quite difficult because the plastic substrate flexes and bends quite easily. The temporary carrier wafer allows one to more easily handle the electrode in the final processing steps before completing device fabrication. Reactive ion etching or inductively coupled etching forms the penetrating electrodes (16 in FIG. 1) of the remaining substrate material 40, that are metal tipped with the metal bi layer of layers 66 and 68, as shown in FIG. 4Q. Metal electrode lines are preferably encapsulated in the polyimde films. The preferred embodiment provides a method for constructing penetrating electrodes utilizing a top-down approach. The bonded sample is etched, e.g., with SF6/C4F8 ICP/RIE plasma, to pattern the silicon penetrating electrodes. The nickel etch mask (metal layer 68) does get attacked by the SF6 plasma. The nickel is resistant to the etch plasma for about an hour and a half etching before nickel starts getting attacked, and is completely removed after about three hours of exposure to the SF6/C4F8 plasma. While it is important for the etch mask to resist the ICP plasma for several hours during the etching process, it can be advantageous if nickel is slightly consumed during this process. This allows for silicon penetrating electrodes to form into points at the tips, which is preferred when the electrode is to be used as an implant as the penetration of the electrodes into cortical tissue is aided by tips. Additionally, small portions of exposed titanium are attacked by the $SF_6$. The dimensions of the nickel etch mask (layer 68) are smaller than the access vias 62 causing there to be a small area of exposed titanium 50 at the substrate 40 to be attacked. This would normally cause the device to be open circuited because the silicon electrode 40 would not be in electrical contact with the rest of the electrode line, but the sandwiched nickel layer protects the underlying titanium and makes electrical contact to the silicon electrode above it. In FIG. 4Q, it is apparent that a small portion of titanium is exposed because the via opening is larger than the electrode. The Ni protects the exposed titanium surrounding the electrode from being etched away completely. While there are some constraints to the limit that the silicon penetrating electrodes of actual devices can be scaled down to, experiments demonstrated aspect ratios greater than 18:1 and penetrating electrode diameters less than three microns can be achieved. This result suggests the etching will not constrain scaling the device down further.

Figure 4R:
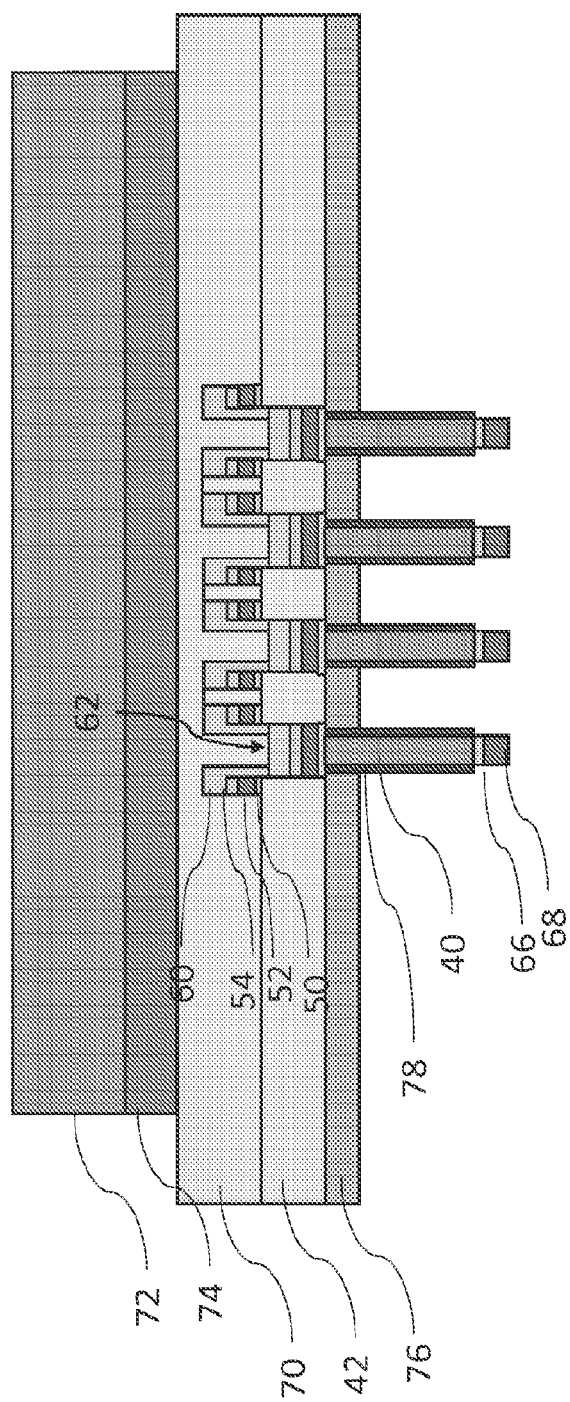
Figure 4S:
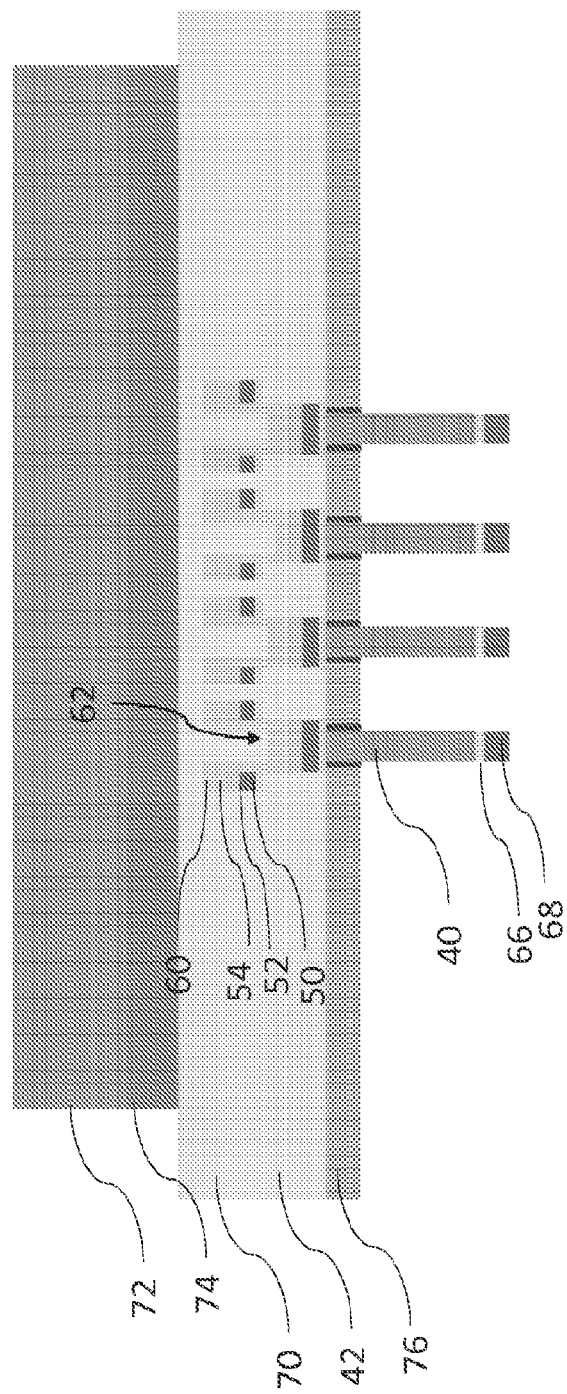
Figure 4T:
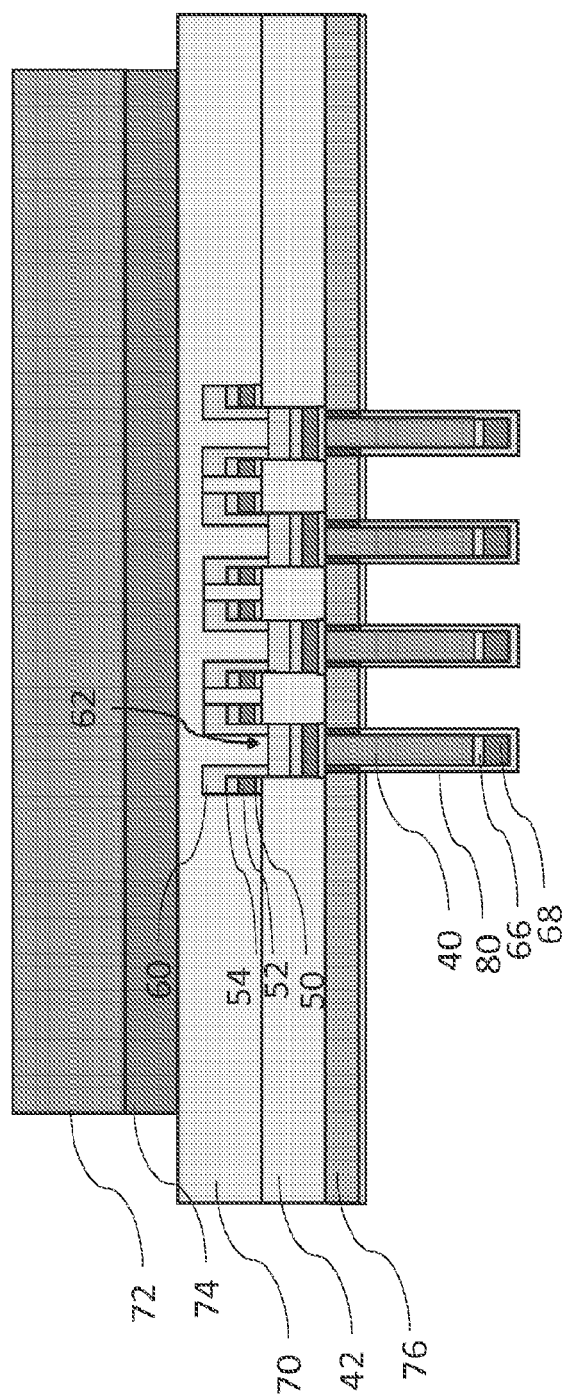
Figure 4U:
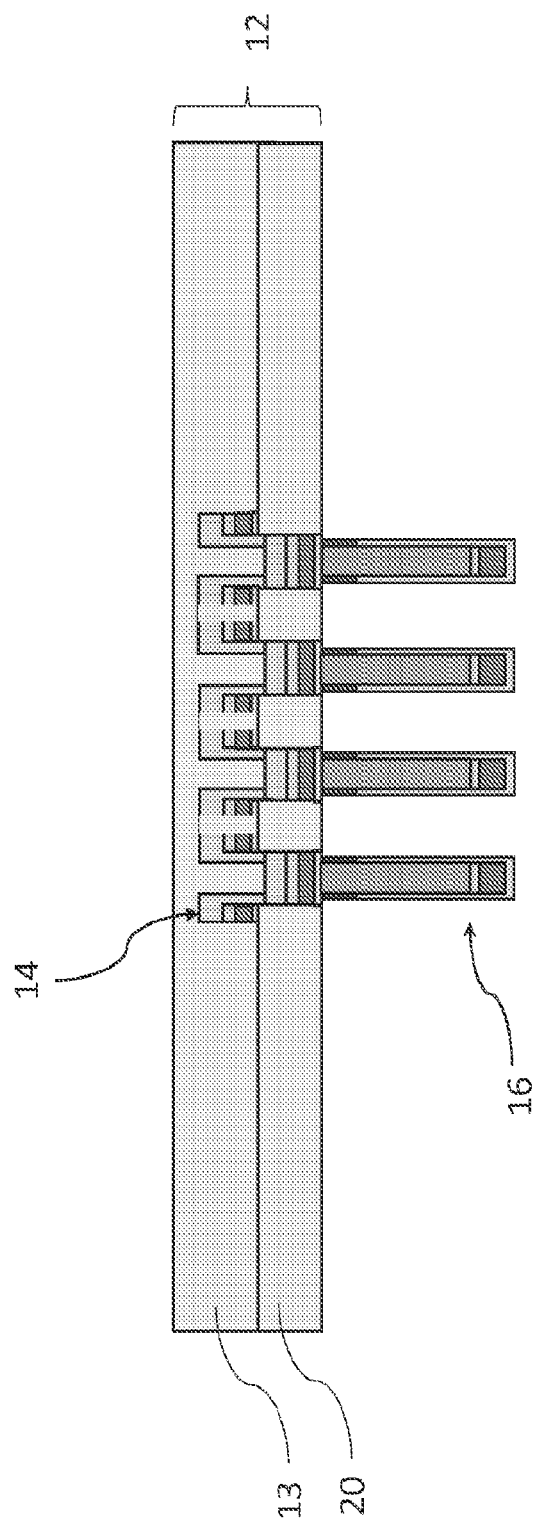

This etching does not affect the already formed electrode lead lines, because the lines are protected by the plastic 42 that forms the passivation layer 20 of FIG. 1 and additional plastic 70 that forms the lower part of the substrate 13 in FIG. 1. In FIG. 4R, a protective layer 76, such as PMMA is formed. FIG. 4R also illustrates native oxide that forms on the substrate material 40 of the penetrating electrodes. The protective layer protects the plastic layer 42 during an etching process to remove the native oxide, e.g. $SiO_2$ in the case of a silicon substrate. The result of the etching process, conducted for example with diluted BOE (buffered oxide etching), is shown in FIG. 4S. FIG. 4T then shows the result of metal deposition, preferably Ti, preferably via sputtering to form a metal coating 80 that encapsulates the penetrating electrodes, including the semiconductor material 40 and the metal cap formed from layers 66 and 68. In a preferred example experiment, directional sputtering deposited 15 nm of Ti. Other metals can be employed as the encapsulation, such as Pt, but the sputtered Ti was found in experiments to provides for an easier more reliable lift-off of the protective layer 76. Ti is therefore the preferred metal for encapsulation of the penetrating electrodes. Lift off of the photoresist 74 and the protective layer 76, shown in FIG. 4U, provides the completed penetrating electrode flexible sensor array of FIG. 1. The completed structure of FIG. 4U is labelled with reference numerals from FIG. 1 to identify the result of the FIGS. 4A-4U preferred fabrication process.

Figure 5A:
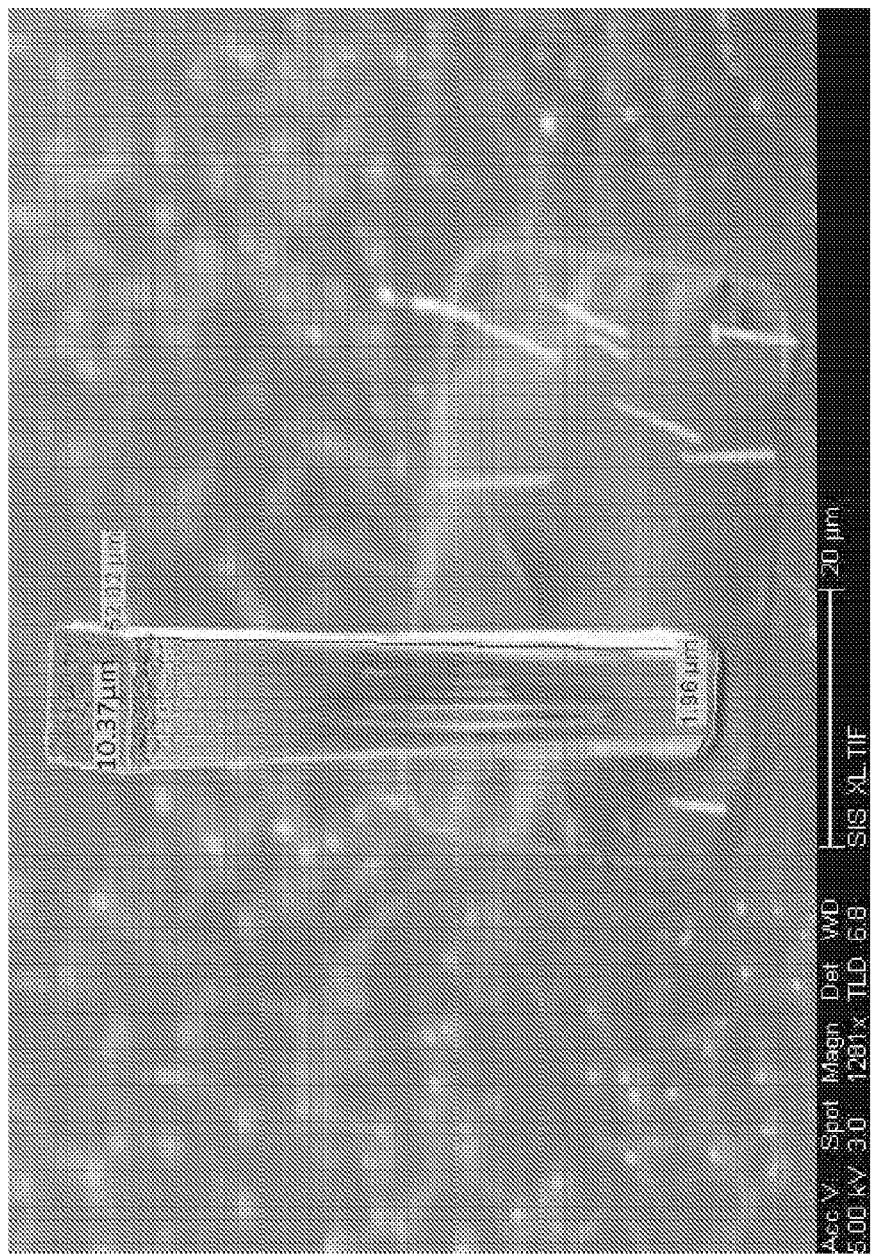
FIGS. 5A-5D are SEM images of example penetrating conformal multi electrode sensor arrays of the invention.
Figure 5B:

Experiments fabricated various penetrating electrode flexible sensor arrays according to the process of FIGS. 4A-4U. FIG. 5A is an SEM image of a single Si penetrating electrode aligned and electrically connected through a via to a metal electrode line underneath. The example electrode was measured to by 52.82 µm high. The height of the electrode is determined by the thickness of the semiconductor substrate 40, and other heights can be produced with substrates. In particularly preferred embodiments, the height of the penetrating electrodes measured from the conformal flexible substrate is in the range of ~30-120 µm, and especially ~70-100 µm. The example penetrating electrode was slightly narrower at the base, measured as 7-8 µm with the top being 10.37 µm. The base of the electrode was about 7-8 µm (not labelled). As discussed above, the length of the etching process to form the penetrating electrodes and the thickness of the metal layer 68 can be selected such that the metal layer 68 is partially consumed to provide a pointed end to the penetrating electrode, which is advantageous. The electrode in FIG. 5A has a generally square cross section. The cross sectional shape of the electrode can be altered and is determined by the etching process of FIG. 4O-4U. To vary the shape of the penetrating electrode, different etching mask designs can be utilized to achieve various shaped penetrating electrodes, e.g. round, triangular cross sections. FIG. 5B is another SEM image is of a Si penetrating electrode on a flexible film under bending stress. The example electrode has height of ~70 μm, and the Si penetrating electrode remains in tact, connected to the flexible plastic thin film and to the electrode lines after flexing the film with a large radius of curvature as shown FIG. 5B.

Figure 5C:
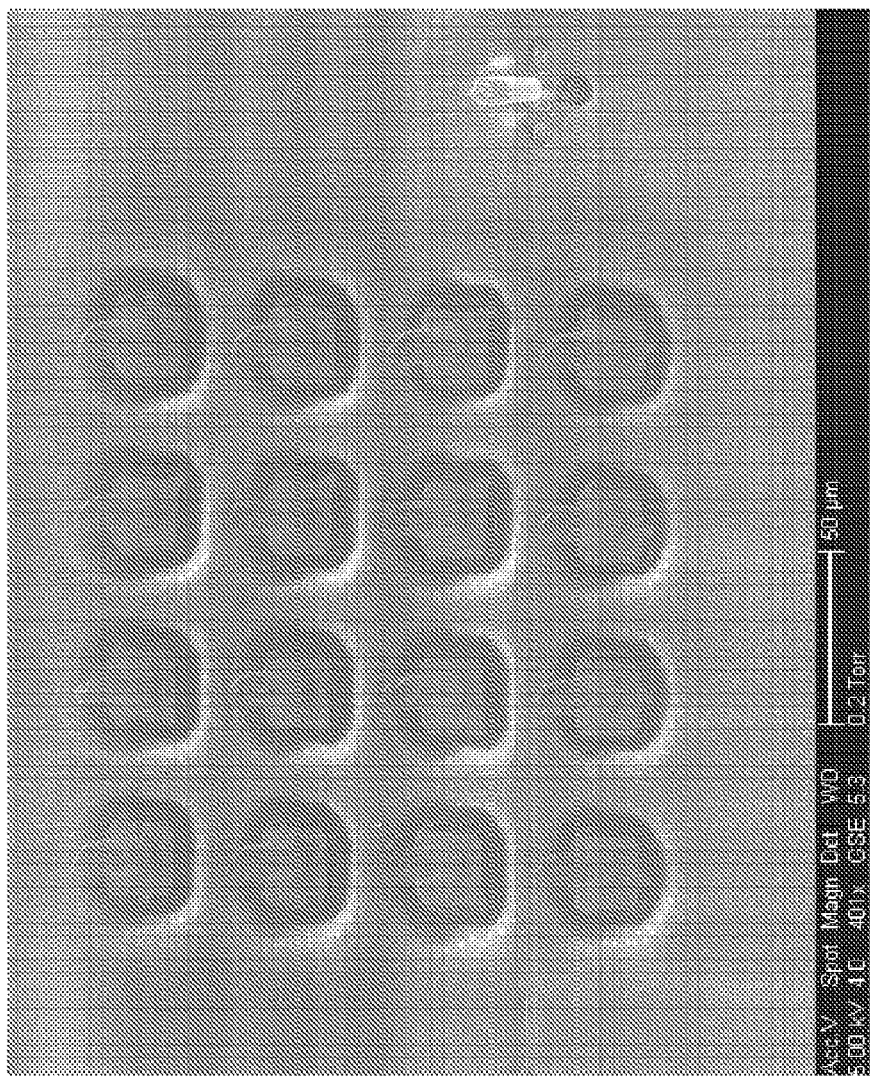
Figure 5D:
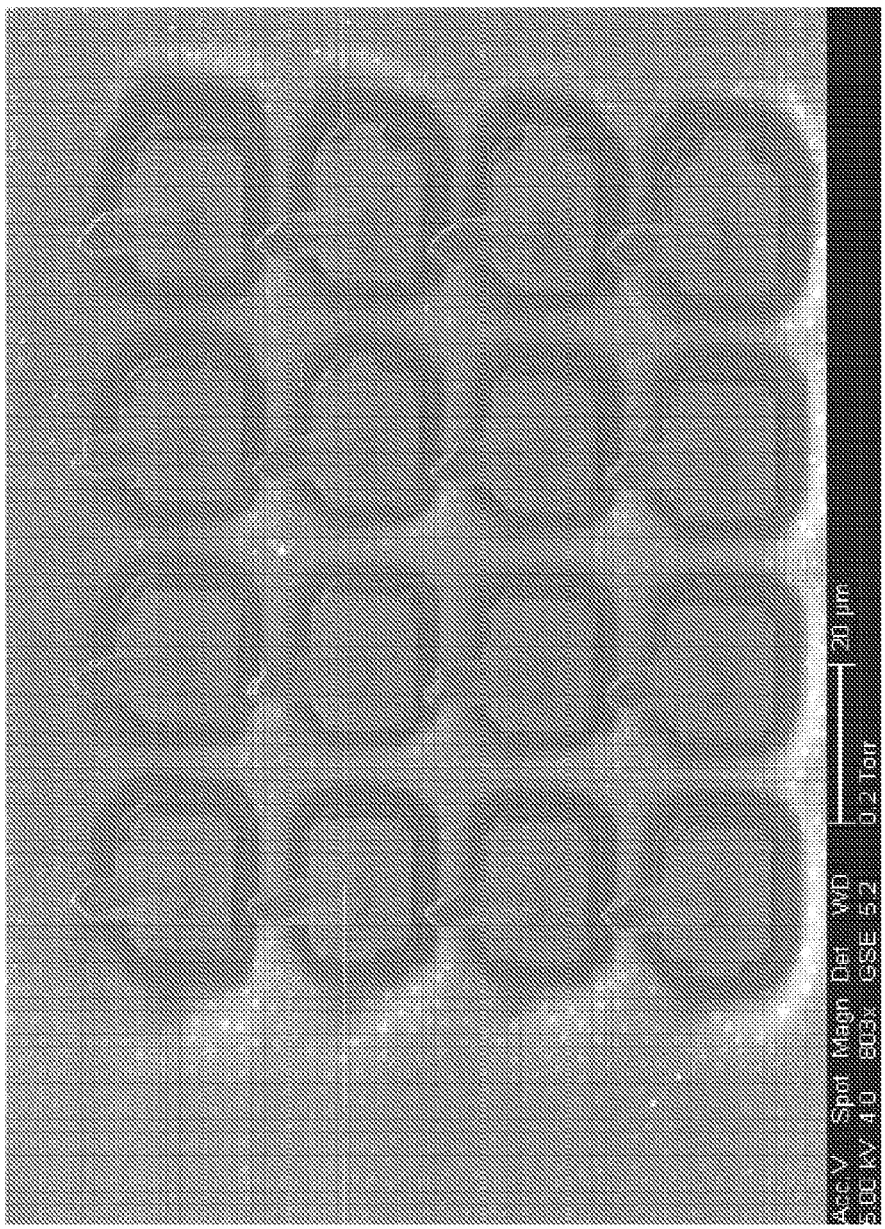

FIGS. 5C and 5D are respective experimental 4×4 square arrays of penetrating electrodes and a flexible conformal plastic substrate. The FIG. 5C example shows penetrating electrodes with 50 μm pitch, and FIG. 5D with a 25 μm pitch between penetrating electrodes. The FIGS. 5C and 5D SEM micrographs were taken prior to platinum sputter coating of the penetrating electrodes. A sacrificial electrode is also visible in the lower right portion of FIG. 5C.

Figure 6:
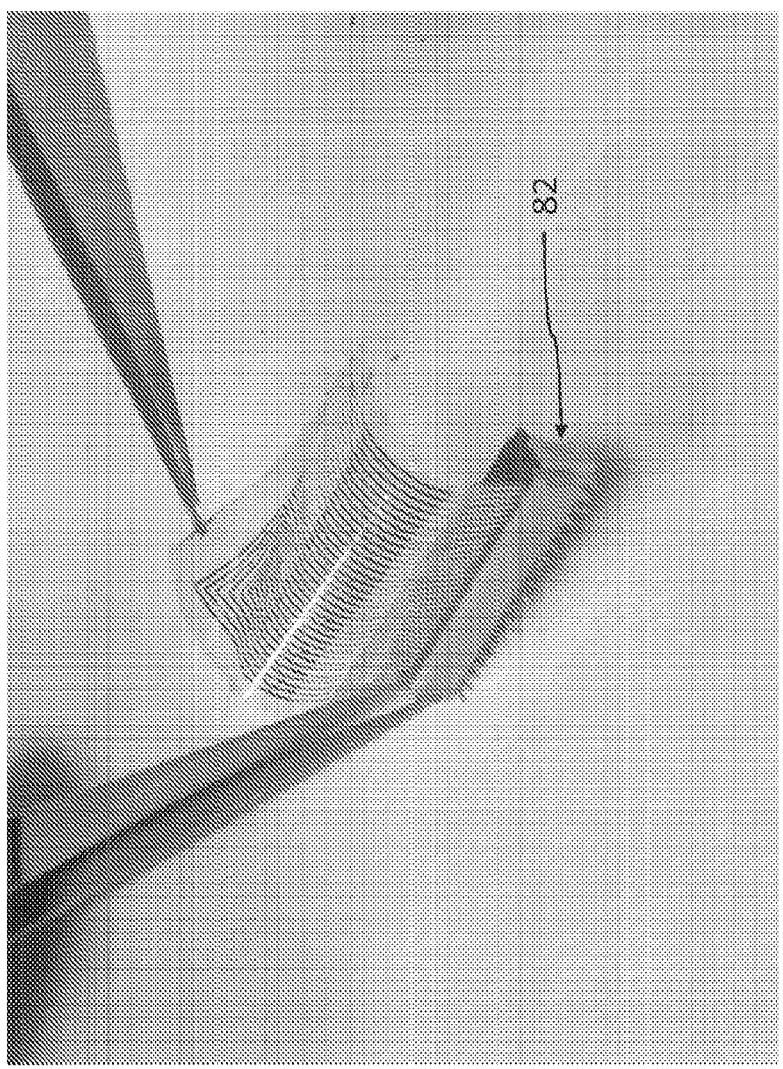
FIG. 6 shows a preferred embodiment penetrating conformal multi electrode sensor arrays of the invention connected to an electrode clip.

FIG. 6 shows an image of an experimental penetrating conformal sensor array being bent and held with tweezers and connected to an electrode clip 82. The clip 80 is a zero insertion force clip, and permits reading from a sensor array that is implanted onto cortical tissue. The flexibility of the array is such that it conforms to cortical tissue.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention.

Various features of the invention are set forth in the appended claims.

The invention claimed is:

1. A method for forming a multielectrode conformal penetrating array, the method comprising:
   providing a semiconductor substrate having a thickness corresponding to a height of penetrating semiconductor micro electrodes to be formed;
   coating a face of the semiconductor substrate with a flexible material in a thickness corresponding to a flexible substrate to be formed;
   patterning the flexible material for vias;
   patterning and forming electrode lines on the flexible material and contact pads through the vias;
   patterning an opposite face of the semiconductor substrate; and etching away the semiconductor substrate to leave a pattern of a two-dimensional array of the penetrating semiconductor micro electrodes extending away from the flexible substrate formed by the flexible material that is exposed after etching away the semiconductor substrate to leave the pattern of the two-dimensional array of the penetrating semiconductor micro electrodes extending perpendicularly from the flexible substrate.

2. The method of claim 1, wherein the flexible material and the flexible substrate comprise polyimide.

3. The method of claim 1, wherein the semiconductor substrate and the penetrating semiconductor micro electrodes comprise silicon.

4. The method of claim 1, wherein said etching away uses a mask that is resistant to etching for part of the etching away and becomes etched during a final portion of the etching away to form the penetrating semiconductor micro electrodes with pointed tips.

5. The method of claim 4, further comprising depositing metal prior to said etching away, wherein the pointed tips include the metal that is deposited prior to said etching away.

6. The method of claim 1, further comprising encapsulating the penetrating semiconductor micro electrodes with metal.

7. The method of claim 1, wherein a pitch between individual ones of the penetrating semiconductor micro electrodes is in the range of 25-200 μm.

8. The method of claim 7, wherein a pitch between individual ones of the penetrating semiconductor micro electrodes is in the range of 25-50 μm.

9. The method of claim 1, wherein the flexible substrate has a total thickness in the range of ~7-15 μm.

10. The method of claim 1, wherein said patterning and etching away leaves a square pattern of the penetrating semiconductor microelectrodes.

11. The method of claim 1, wherein the thickness of the semiconductor substrate and the height of semiconductor micro electrodes is ~30-120 μm.

12. The method of claim 11, wherein the thickness of the semiconductor substrate and the height of said semiconductor micro electrodes is ~70-100 μm.

13. The method of claim 1, wherein said flexible material comprises plastic.

14. The method of claim 13, wherein said flexible material comprises polyimide.

15. The method of claim 1, further comprising depositing an additional layer of flexible material over said electrode lines prior to said patterning an opposite face.

16. The method of claim 1, further comprising encapsulating the penetrating semiconductor micro electrodes.

* * * * *